(12) United States Patent
Arlow et al.

(10) Patent No.: US 8,151,791 B2
(45) Date of Patent: Apr. 10, 2012

(54) METHODS AND DEVICES FOR PERFORMING AN EMERGENCY OR NON-EMERGENCY TRACHEOTOMY

(75) Inventors: Richard L Arlow, Southampton, NJ (US); Zachary W Bloom, Mamaroneck, NY (US); Brian H Buchholz, Hampstead, NH (US)

(73) Assignee: Lifeserve Innovations, LLC, Bethlehem, PA (US)

( * ) Notice: Subject to any disclaimer, the term of this patent is extended or adjusted under 35 U.S.C. 154(b) by 554 days.

(21) Appl. No.: 12/431,803

(22) Filed: Apr. 29, 2009

(65) Prior Publication Data

US 2010/0275911 A1 Nov. 4, 2010

(51) Int. Cl.
*A61M 16/00* (2006.01)
*A62B 9/06* (2006.01)
(52) U.S. Cl. .......... 128/200.26; 128/207.14; 128/207.29
(58) Field of Classification Search ............. 128/200.24, 128/200.26, 207.14–207.15, 207.29; 604/104, 604/117, 164.09, 164.1, 164.11; *A61M 16/00; A62B 9/06*
See application file for complete search history.

(56) References Cited

U.S. PATENT DOCUMENTS

| | | | |
|---|---|---|---|
| 2,991,787 A * | 7/1961 | Hunter et al. | 128/207.17 |
| 3,384,087 A * | 5/1968 | Brummelkamp | 128/207.29 |
| 4,331,138 A | 5/1982 | Jessen | |
| 4,405,314 A | 9/1983 | Cope | |
| 4,438,768 A | 3/1984 | Barrickman | |
| 4,520,810 A | 6/1985 | Weiss | |
| 4,556,059 A * | 12/1985 | Adamson, Jr. | 128/207.29 |
| 4,643,188 A | 2/1987 | Weiss | |
| 4,677,978 A | 7/1987 | Melker | |
| 4,969,454 A | 11/1990 | Servello | |
| 4,978,334 A * | 12/1990 | Toye et al. | 604/506 |
| 5,058,580 A | 10/1991 | Hazard | |
| RE34,086 E * | 10/1992 | George | 128/200.26 |
| 5,217,005 A | 6/1993 | Weinstein | |
| 5,217,007 A | 6/1993 | Ciaglia | |
| 5,279,285 A | 1/1994 | Griggs | |

(Continued)

FOREIGN PATENT DOCUMENTS

WO WO2008009943 A1 1/2008
(Continued)

OTHER PUBLICATIONS

International Search Report regarding International Application No. PCT/US2010/032076, filed Apr. 22, 2010.

*Primary Examiner* — Oren Ginsberg
(74) *Attorney, Agent, or Firm* — Caesar Rivise Bernstein Cohen & Pokotilow, Ltd.

(57) ABSTRACT

Methods and devices for performing emergency and non-emergency tracheotomies are disclosed. In one embodiment, a device for performing an emergency tracheostomy includes a dilator having a generally curved outer surface which is arranged for insertion into a trachea of a patient. The dilator includes an open linear passageway therein. Situated within the internal passageway is an anchor that includes a distal tip portion protruding outside the dilator. The anchor is normally biased to a retracted position and is arranged to move from the retracted position to an extended position in response to a distal force. A driver is provided for applying the distal force to the anchor to drive the distal tip portion through an opening in the patient's neck and trachea. A method for using the device is also disclosed.

20 Claims, 16 Drawing Sheets

U.S. PATENT DOCUMENTS

| | | |
|---|---|---|
| 5,546,939 A | 8/1996 | French |
| 5,681,323 A | 10/1997 | Arick |
| 5,690,669 A * | 11/1997 | Sauer et al. .................. 606/196 |
| 6,080,173 A | 6/2000 | Williamson, IV et al. |
| 6,109,264 A * | 8/2000 | Sauer ........................ 128/207.29 |
| 6,286,509 B1 * | 9/2001 | Nash et al. ............... 128/207.14 |
| 6,298,851 B1 | 10/2001 | Parota et al. |
| 6,382,209 B1 * | 5/2002 | Toye ........................ 128/207.14 |
| 6,637,435 B2 | 10/2003 | Ciaglia et al. |
| 6,669,708 B1 * | 12/2003 | Nissenbaum et al. ........ 606/153 |
| 6,706,017 B1 * | 3/2004 | Dulguerov ............... 604/164.01 |
| 7,169,129 B2 | 1/2007 | Gooden |
| 7,267,124 B1 | 9/2007 | Roberson, Jr. et al. |
| 7,305,989 B2 | 12/2007 | Gostelow |
| 7,373,939 B1 | 5/2008 | DuBois et al. |
| 2004/0255954 A1 | 12/2004 | Zgoda et al. |
| 2006/0081260 A1 | 4/2006 | Eells et al. |
| 2006/0124134 A1 | 6/2006 | Wood |
| 2007/0246051 A1 | 10/2007 | Newman |
| 2009/0312784 A1 * | 12/2009 | Tupper ........................ 606/191 |

FOREIGN PATENT DOCUMENTS

WO     WO2008034872 A1     3/2008

* cited by examiner

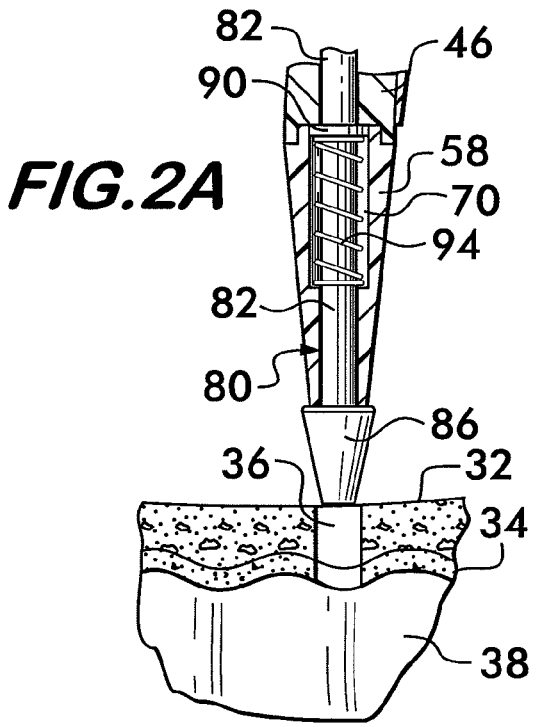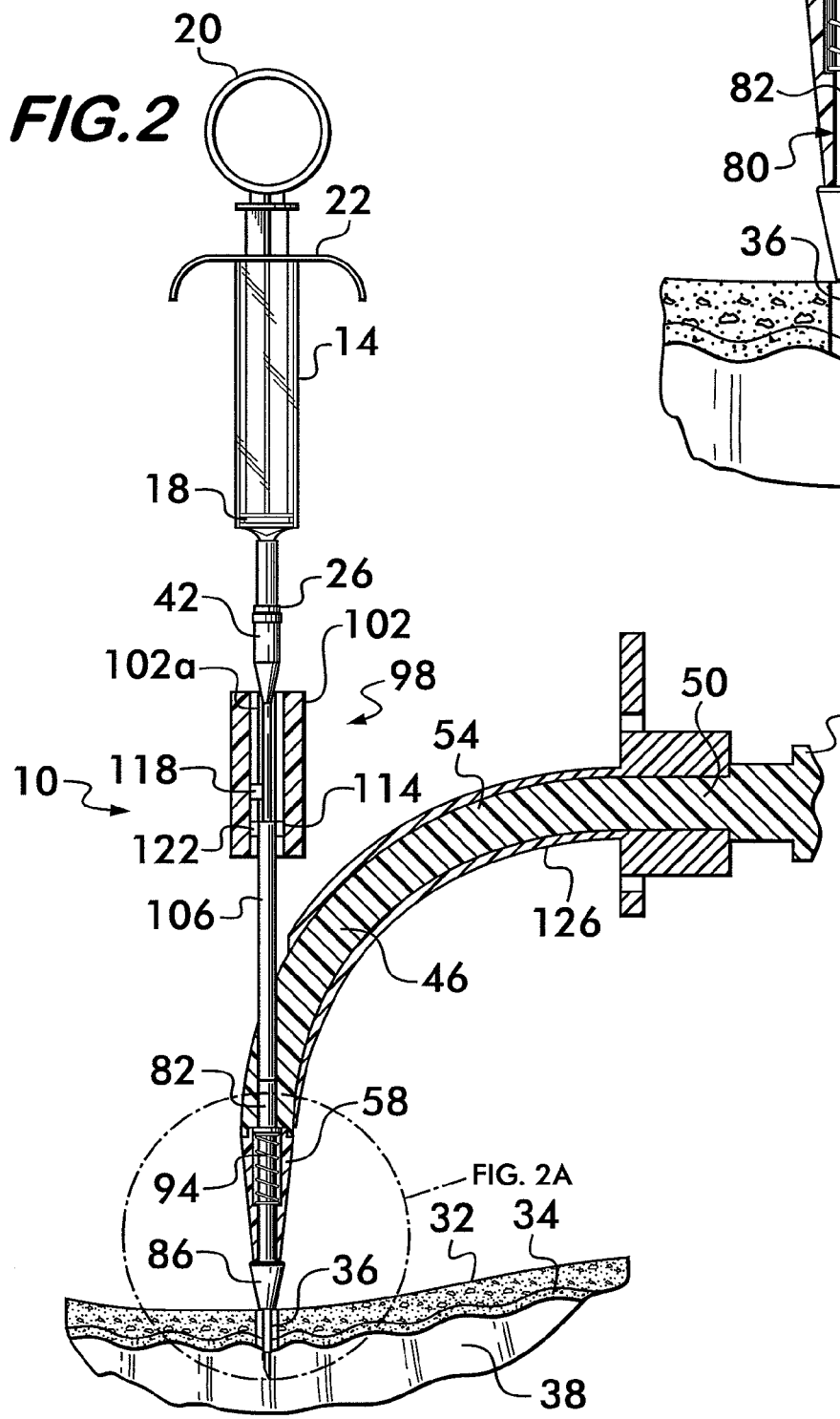

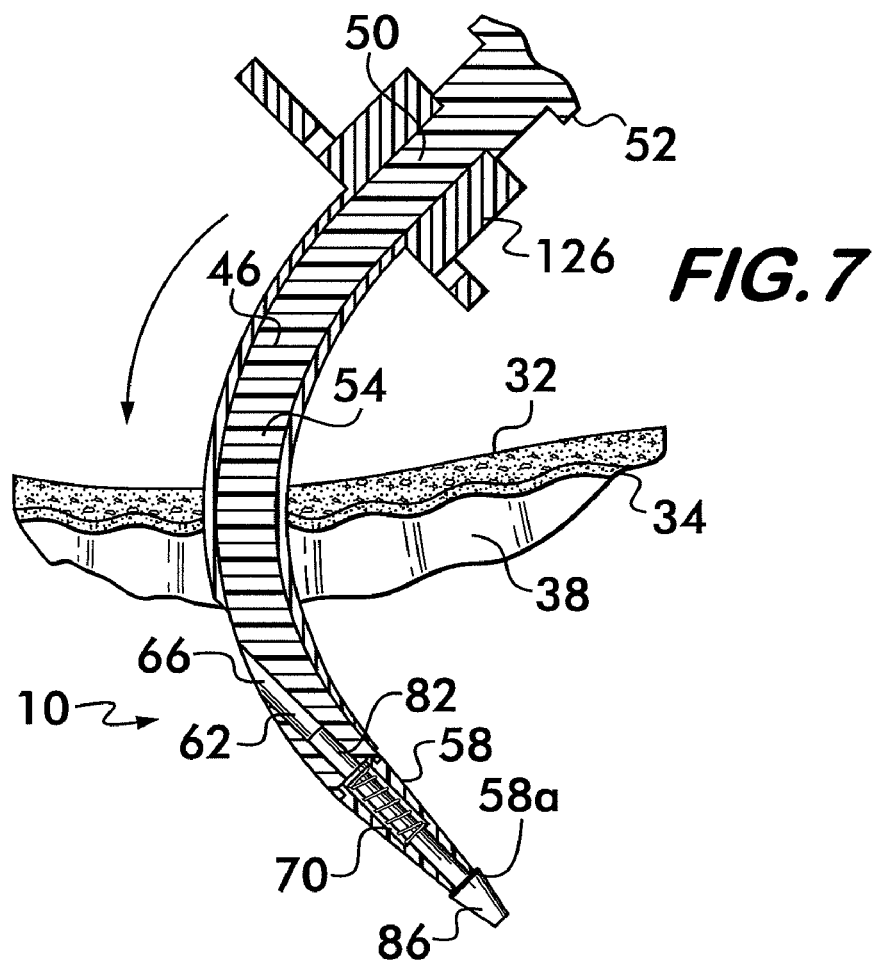
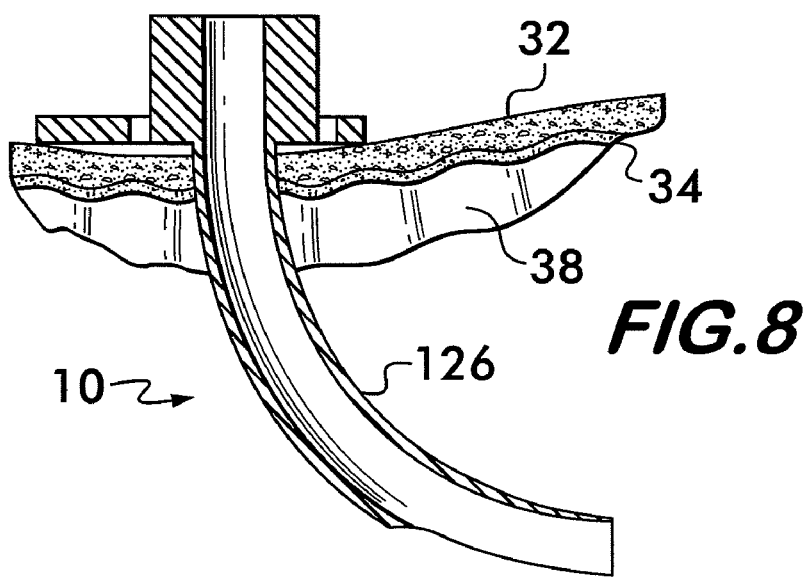

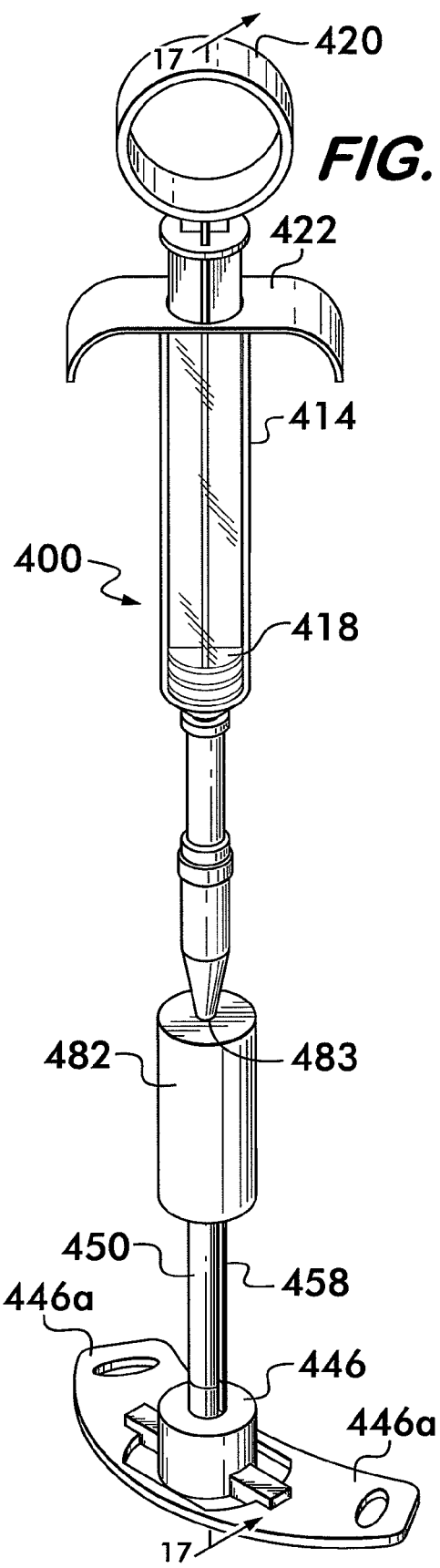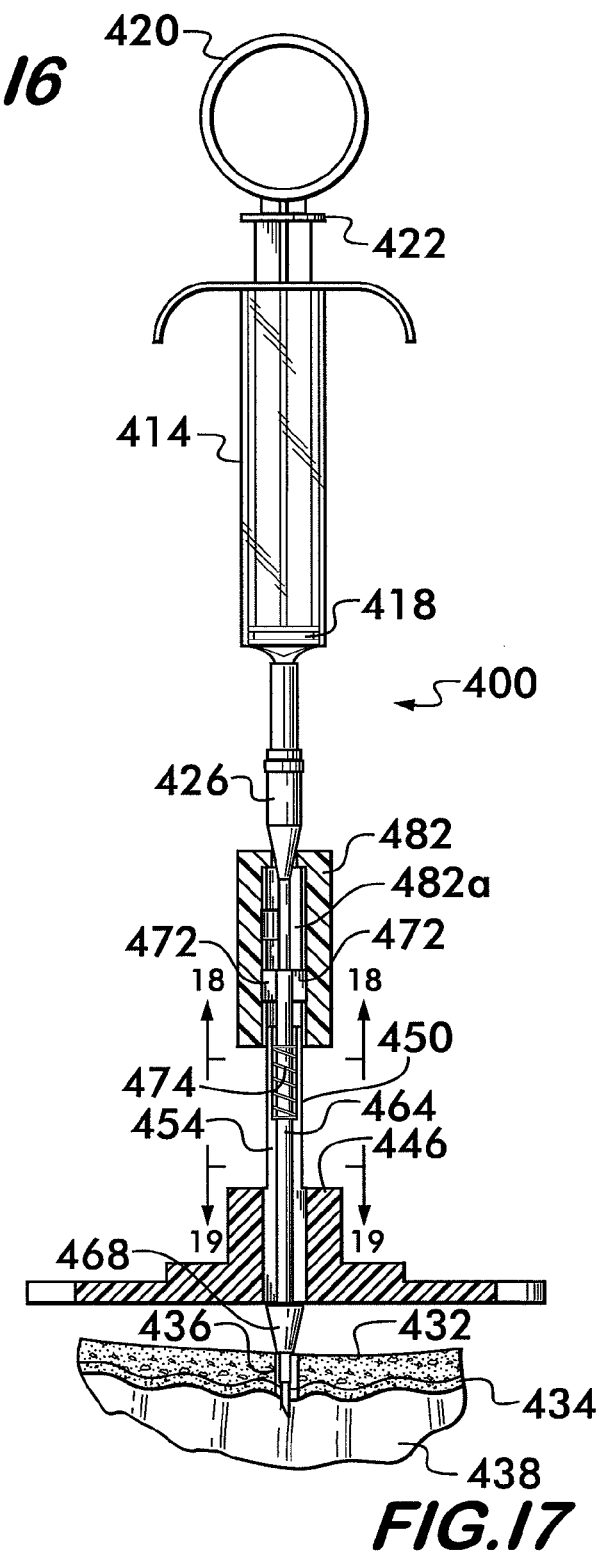

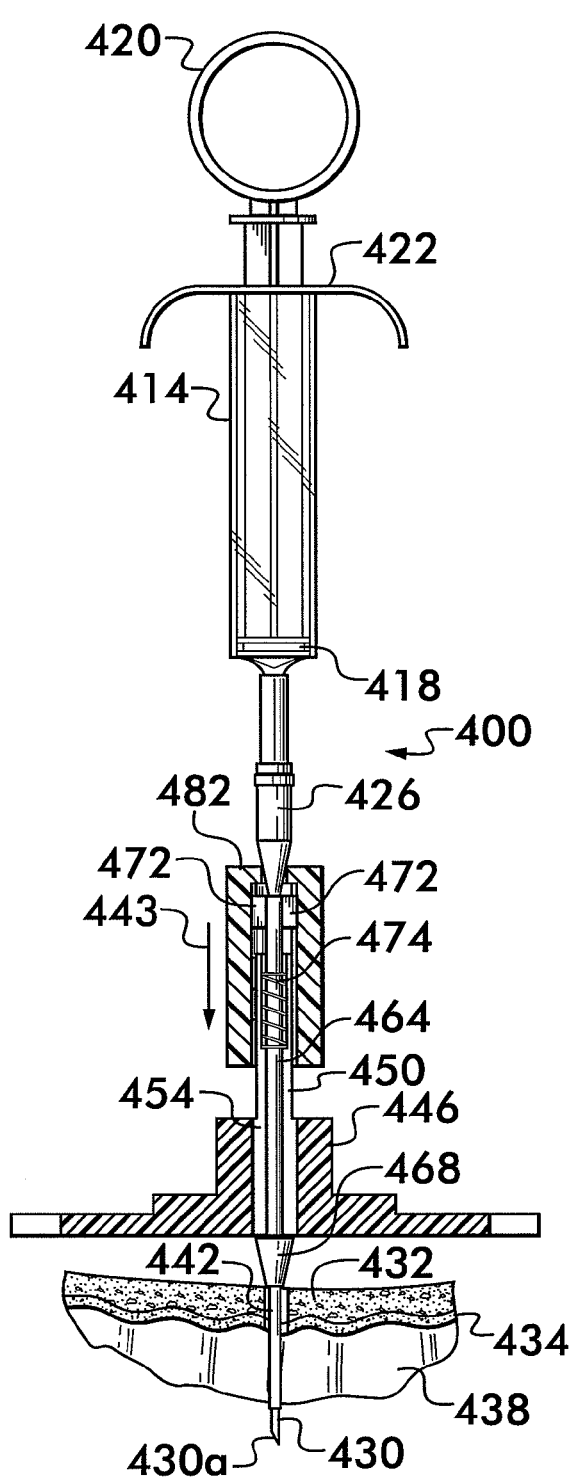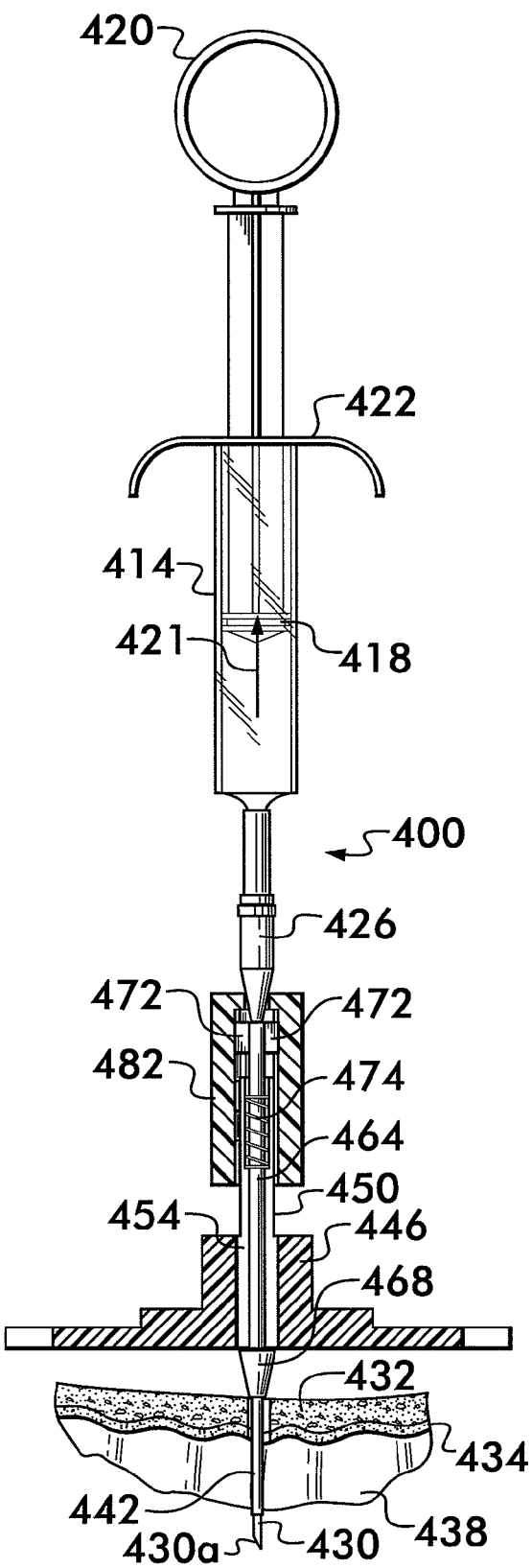
FIG.20
FIG.21

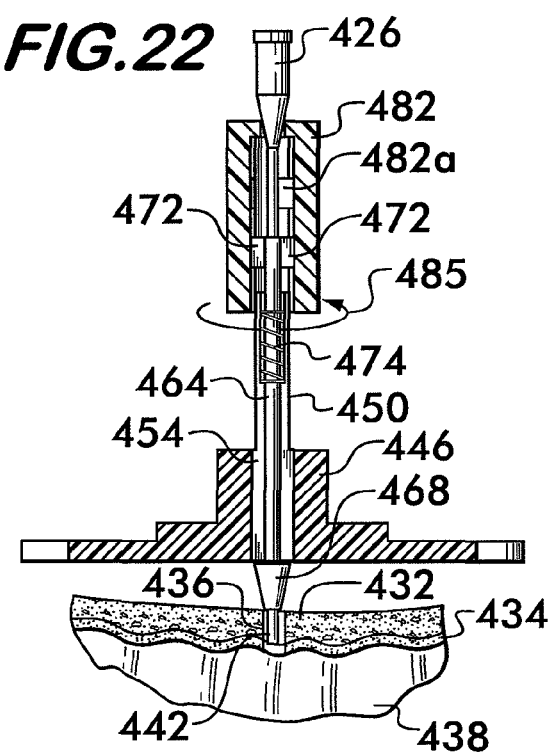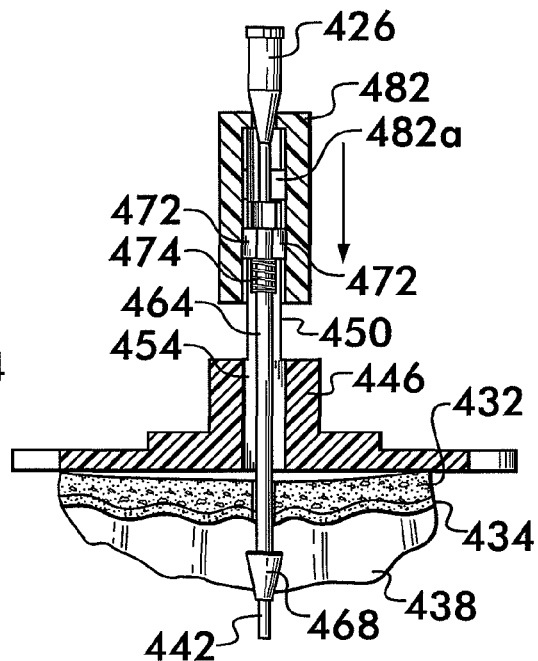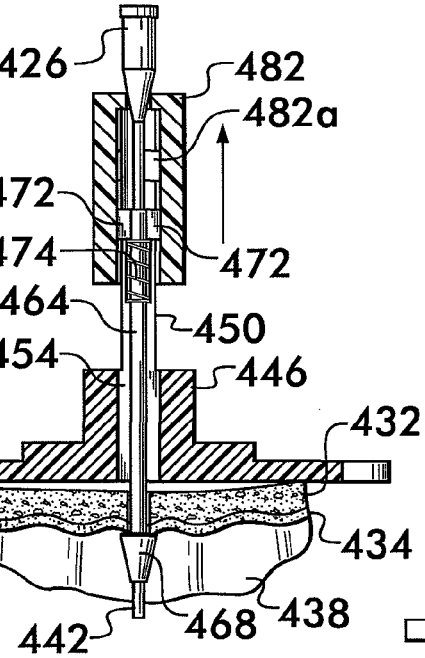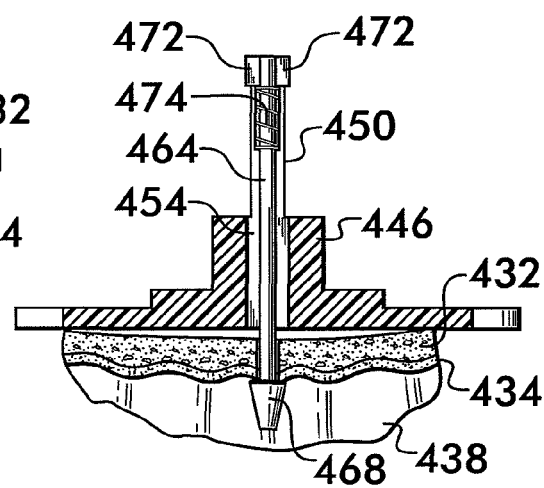

METHODS AND DEVICES FOR PERFORMING AN EMERGENCY OR NON-EMERGENCY TRACHEOTOMY

FIELD OF THE INVENTION

This invention relates generally to medical instruments and methods of their use. More specifically, this invention relates to methods and devices for performing tracheotomies on an emergency or non-emergency basis.

BACKGROUND OF THE INVENTION

In the field of emergency medicine, establishing an airway is often the first step in saving a life. The default procedure for creating an airway is endotracheal intubation by which a tube is inserted through the mouth and into the trachea. When endotracheal intubation is unsuccessful or impossible due to severe head or neck trauma, then an airway can be established surgically by inserting a tube directly into the trachea through the front of the neck. This procedure is commonly known as a tracheotomy. Emergency tracheotomies are a last resort effort to create an airway, and therefore their success is usually critical to patient survival.

Although commonly known as a tracheotomy, there are in fact two different surgical airway procedures: tracheostomies and cricothyroidotomies. The latter is presently the standard practice in emergency medicine. A percutaneous procedure by means of the Seldinger Technique is generally regarded as the safest method for performing a cricothyroidotomy. It involves inserting an airway tube through the cricothyroid membrane, which lies just below the thyroid cartilage (the Adam's apple in men). In this technique, the cricothyroid membrane is palpated between the thyroid and cricoid cartilages. An incision is made in the cricothyroid membrane. An over-the-needle catheter is placed over a hollow needle and the needle and catheter are together inserted into the trachea through the incision with an attached syringe remaining outside of the trachea. The needle is then aspirated by applying back pressure on the syringe to confirm that it is within the trachea. The needle and syringe are then removed with the catheter remaining within the trachea. A guide wire is then fed through the catheter into the airway and the catheter is then removed. A dilator is then fed over the guide wire to dilate the opening to permit spontaneous inhalation and exhalation.

Although only used in last resort efforts to form an airway, emergency cricothyroidotomies have a dangerously high rate of complications including excess time to complete the procedure, incision error including inability to identify the cricothyroid membrane, inappropriateness for children under a certain age, burn or infection at the incision site, tube misplacement, hemorrhaging, and cartilage injury. Often, the unprotected sharp end of a needle utilized during a cricothyroidotomy is inserted too far into the trachea puncturing the soft posterior wall causing injury and severe complications. Also, there is a risk that the needle will not be inserted to the correct depth, because of variations in thickness of neck tissue overlying the trachea. If the needle is not inserted far enough, its tip may be located in the anterior tissues surrounding the trachea instead of in the trachea itself. Similar problems and injuries can arise upon introduction of the guide wire. Cricothyroidotomies often result in long term complications, and are often performed incorrectly, causing damage to the larynx, thyroid gland, esophagus, and trachea. Additionally, the airway from the cricothyroidotomy is temporary, lasting only about thirty to forty-five minutes, due to the inability for carbon dioxide to leave the bloodstream efficiently. Thus, when patients enter the hospital with a cricothyroidotomy, doctors must remove it, repair the cricothyroid membrane, and perform a proper tracheostomy. This creates extra work for the hospital and presents additional risk to the patient.

Relatively speaking, the tracheostomy is a lower risk procedure which has a reduced risk of tracheal perforation. Moreover, since the tracheostomy is performed at a location on the neck that is lower than the location for performing a cricothyroidotomy, there are circumstances where injuries would preclude performing a cricothyroidotomy, where performing a tracheostomy may still be appropriate.

Unlike a cricothyroidotomy, a tracheostomy is a definitive airway which is placed directly into the trachea about two centimeters above the sternal notch. Tracheostomies are the desired method of surgical intubation for in-hospital procedures. Despite being a safe and successful in-hospital procedure, no known current techniques or products allow tracheostomies to be performed in the pre-hospital emergency field. For example, the current tracheostomy procedure is not well adapted for conducting in the field because it requires the use of a real-time bronchoscopic visualization during the procedure to ensure that the needle is not being inserted through the posterior tracheal wall and possibly into the esophagus.

In the pre-hospital emergency field, the cricothyroidotomy is the preferred method because access to the trachea is obtained through the cricothyroid membrane, which is a single small piece of tissue. By contrast, in a tracheostomy, access to the trachea is more difficult requiring breaking through the skin and a layer of cartilage. The tracheostomy is more complex than the cricothyroidotomy requiring a higher level of skill, and requiring the stable environment of an operating room.

The ability to perform emergency tracheostomies in the field prior to the patient's arrival at the hospital will address the risks of current cricothyroidotomies by dramatically reducing steps and complexity, increasing patient safety, increasing ease of use, and decreasing risk of infection. Having the option to perform emergency tracheostomies in the field should increase confidence in emergency responders who previously may not have felt comfortable with the current cricothyroidotomy procedure. Finally, performing emergency tracheostomies in the field will eliminate the need for redundant surgical intubation in the hospital and will likely decrease the high complication rate of emergency cricothyroidotomies.

BRIEF SUMMARY OF THE INVENTION

Methods and devices for performing emergency and non-emergency tracheotomies are disclosed. In one embodiment, the device is for performing a tracheostomy and includes a dilator having a distal end arranged for insertion into a trachea of a patient, a proximal end arranged to remain outside the trachea, and a generally curved outer surface. The dilator includes an internal linear passageway that is open at both ends. Situated within the internal passageway of the dilator is an anchor that includes a distal tip portion protruding outside the dilator. The anchor is normally biased to a retracted position and arranged to move from said retracted position to an extended position in response to a distal force. A driver is provided for applying the distal force to the anchor to drive the distal tip portion through an opening in the patient's neck and trachea. A method is disclosed describing use of the tracheostomy device on a patient. Other methods and devices are disclosed for performing emergency and non-emergency tracheostomies and cricothyroidotomies.

BRIEF DESCRIPTION OF THE DRAWINGS

The invention will be described in conjunction with the following drawings in which like reference numerals designate like elements and wherein:

FIG. 2 is a sectional view taken along lines 2-2 of FIG. 1;

FIG. 2A is an enlarged view of an encircled portion of FIG. 2, labeled "FIG. 2A";

FIG. 7 is an elevational view, mostly in section, of the dilator and tracheostomy tube components of a tracheostomy device of the present invention advanced into the opening in the trachea of the patient;

FIG. 8 is an elevational view, in section, of a tracheostomy tube component of a tracheostomy device of the present invention advanced into the opening in the patient's trachea;

FIG. 16 is a perspective view of a device for performing a tracheostomy of the present invention;

FIG. 17 is a sectional view taken along lines 17-17 of FIG. 16;

FIG. 20 is an elevational view, partially in section, of a device for performing a tracheostomy of the present invention;

FIG. 21 is an elevational view, partially in section, of a device for performing a tracheostomy of the present invention illustrating aspiration of the needle extending into the trachea of a patient;

FIG. 22 is an elevational view, partially in section, of a device for performing a tracheostomy of the present invention illustrating the first step of insertion of the anchor into the trachea of a patient;

FIG. 23 is an elevational view, partially in section, of a device for performing a tracheostomy of the present invention illustrating the anchor extending into the trachea of the patient;

FIG. 24 is an elevational view, partially in section, of a device for performing a tracheostomy of the present invention illustrating the anchor extending into the trachea of the patient; and, FIG. 25 is an elevational view, partially in section, of a device for performing a tracheostomy of the present invention illustrating the anchor protruding into the trachea of the patient.

DETAILED DESCRIPTION OF THE INVENTION

Figure 3:
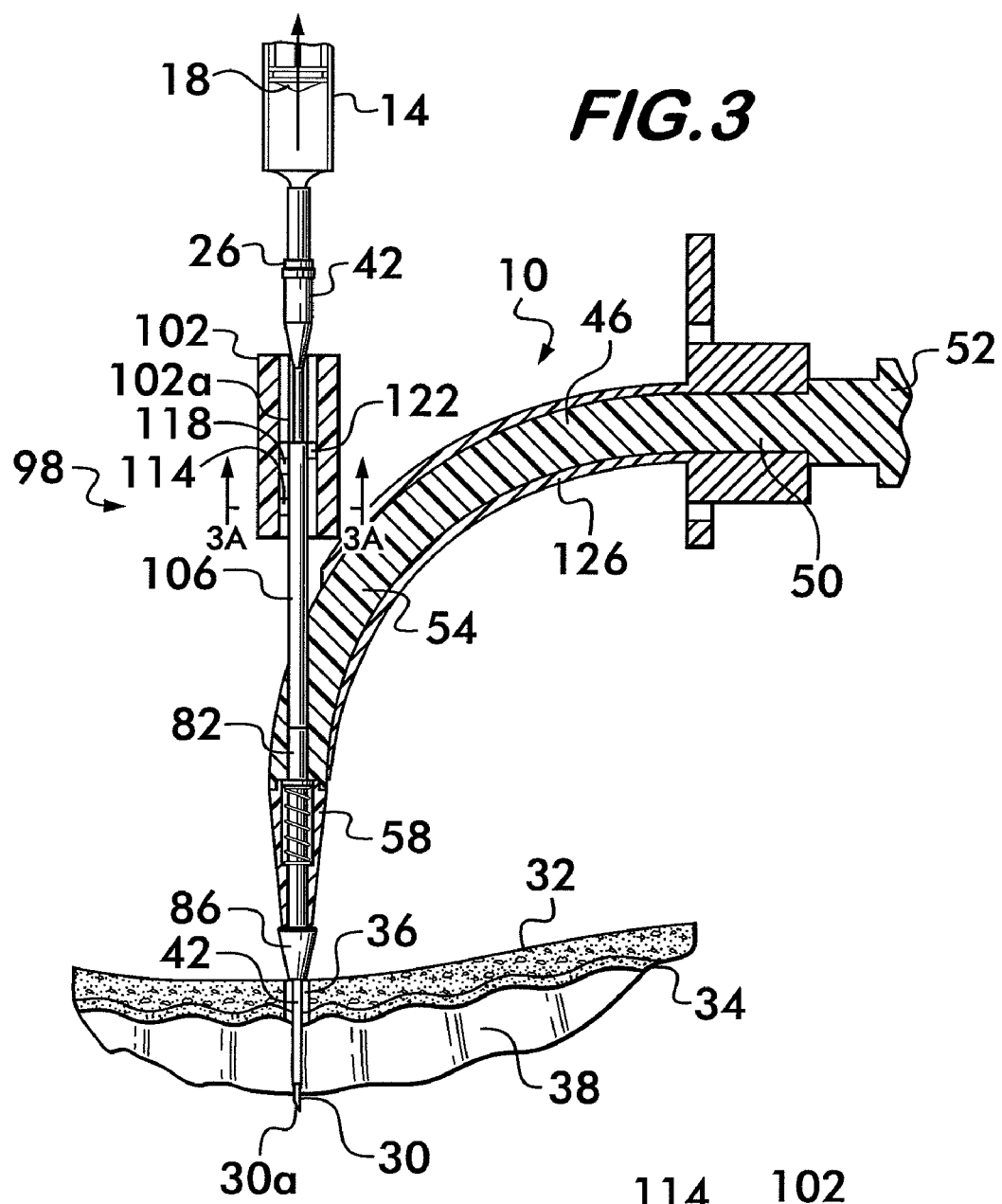
FIG. 3 is an elevational view, partially in section, of a device for performing a tracheostomy of the present invention illustrating the needle and catheter protruding into the trachea of a patient and aspiration of the needle.

Referring now in detail to the various figures of the drawings wherein like reference characters refer to like parts, there is shown at 10 in FIGS. 1 through 8, an embodiment of the device for performing an emergency tracheostomy of the present invention. Referring now to FIGS. 2 and 3, the device 10 comprises a syringe 14. The syringe 14 includes movable plunger 18 which is capable of movement along the cylindrical length of the syringe 14. The plunger 18 is also removable from the syringe 14 at end 22 and includes a thumbhold 20 to enable withdrawal of the plunger 18 using the thumb of the same hand that is manipulating the syringe 14. Referring now to FIG. 3, at the other end of the syringe 14, a needle 30 is attached thereto. The needle 30 includes a sharpened distal end 30a to penetrate the skin 32 and cartilage 34 forming the wall of the trachea 38 just above the sternal notch (not shown) at the site of entry where the tracheostomy is performed. Positioned over the needle 30 is a flexible catheter 42, preferably made from teflon or another suitable resilient material. As can be seen from FIG. 3, the catheter 42 is shorter in length than the needle 30 and includes attachment means 26 to fit onto the syringe 14.

Figure 1:
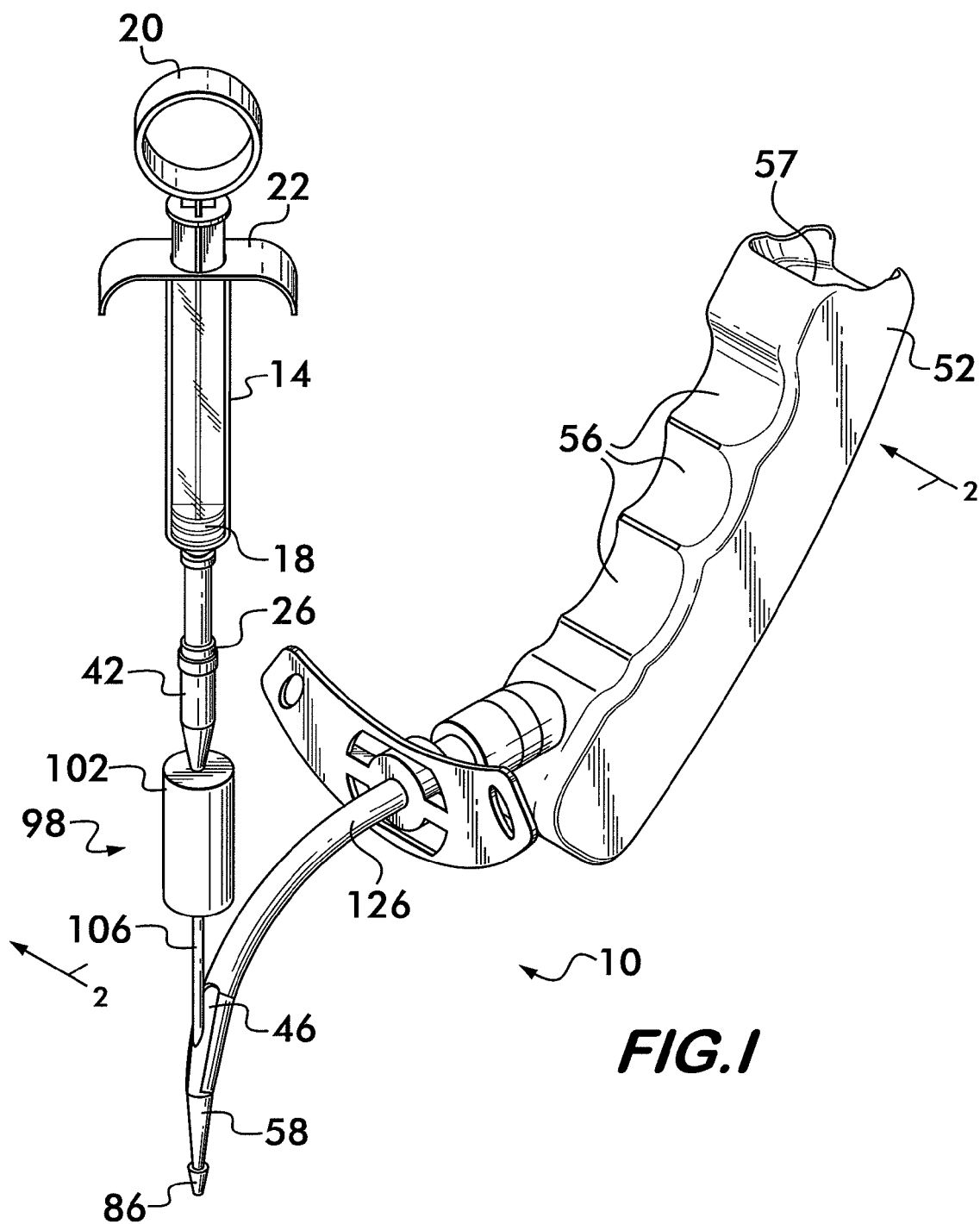
FIG. 1 is a perspective view of a device for performing a tracheostomy of the present invention.

As best shown in FIGS. 2A and 3, after the initial incision is made (approximately 2 centimeters in size) at the site of entry for a tracheostomy using a suitable scalpel, the needle 30 penetrates the skin 32 and trachea wall cartilage 34 of the neck to create an opening 36 therein extending into the trachea 38. As the needle 30 penetrates the skin 32 and trachea wall cartilage 34 and enters the trachea 38, the catheter 42 also penetrates into the trachea 38. Referring now to FIGS. 1 and 3, to affirm that the needle 30 is in the trachea 38, the plunger 18 may be withdrawn utilizing the thumbhold 20 to determine the nature of the material at the needle tip 30a. If little or no blood is drawn into the chamber of the syringe 14 and there is aspiration of air, it can be assumed that the needle tip 30a is positioned correctly within the trachea 38.

The embodiment 10 also includes a tracheostomy dilator 46, which is shown in FIGS. 1-7. Referring now to FIGS. 2 and 2A, the tracheostomy dilator 46 includes a proximal end 50 which is arranged for attachment to a handle 52, such as when parts of the device 10 are being provided in kit form. Alternatively, the tracheostomy dilator 46 and handle 52 may be of integral construction. As shown in FIG. 2, the tracheostomy dilator 46 includes a curved body portion 54 that extends from the proximal end 50 to a tapered piece 58. The curved body portion 54 is shown as being of uniform cross-section, but may be constructed of other geometries, e.g., tapered, without departing from the scope of this invention.

Figure 6:
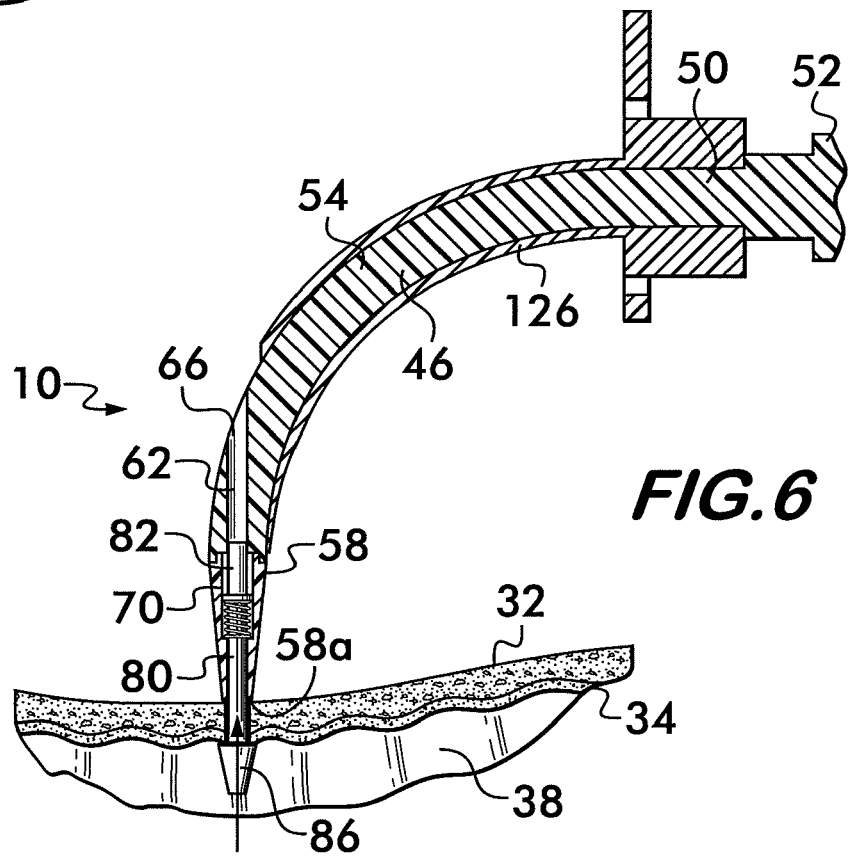
FIG. 6 is an elevational view, partially in section, of a device for performing a tracheostomy of the present invention illustrating the anchor protruding into the trachea of the patient.

As best shown in FIG. 6, the curved shaft 54 includes an internal passageway 62 which extends from the tapered piece 58 linearly upwardly to an opening or port 66 located on the outer surface of the curved body portion 54. The tapered piece 58 is shown as a separate component arranged for attachment at the distal end of the curved body portion 54, but may be integral therewith. The tracheostomy dilator 46 may be hydrophobically coated or coated with a suitable surgical lubrication.

Figure 5:
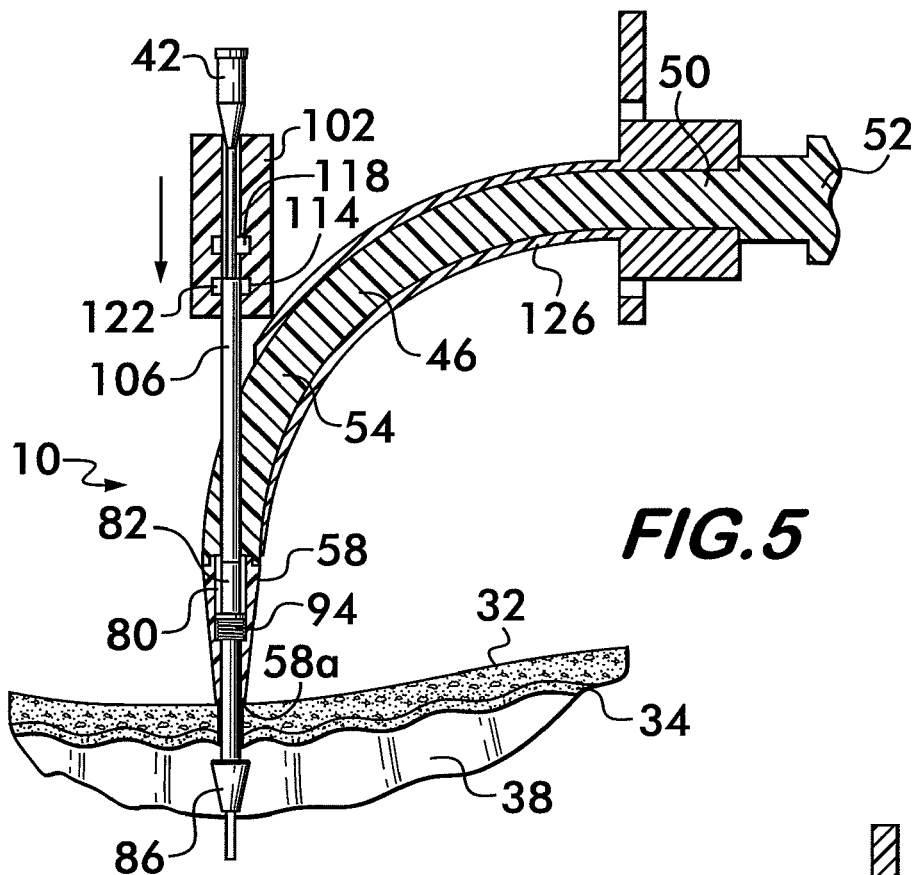
FIG. 5 is an elevational view, partially in section, of a device for performing a tracheostomy of the present invention illustrating the anchor protruding into the trachea of the patient.

As best shown in FIGS. 5 and 6, the tapered piece 58 extends linearly and tapers towards an opening 58a located in the distal end thereof. As best shown in FIGS. 2A, 6 and 7, the tapered piece 58 includes a generally cylindrical internal cavity 70 which at its upper end is in communication with the internal passageway 62 of the curved body portion 54 (FIG. 6), and at its distal end is in communication with the opening 58a (FIG. 6). Referring again to FIG. 2A, housed within the internal cavity 70 is a tracheal anchor 80 including a linear shaft 82 which as best shown in FIG. 6 extends from the internal passageway 62 of the curved body portion 54, through the internal cavity 70 of the tapered piece 58 and through the opening 58a at the distal end thereof. Attached at the distal end of the linear shaft 82 is a conical-shaped anchor tip 86 that is arranged for insertion through the opening 36 in the neck and into the trachea 38. Referring now to FIG. 3, the tracheal anchor 80 is provided with an open internal channel (not shown) that runs axially along its entire length to allow passage of the needle 30 and catheter 42 therethrough.

Figure 4:
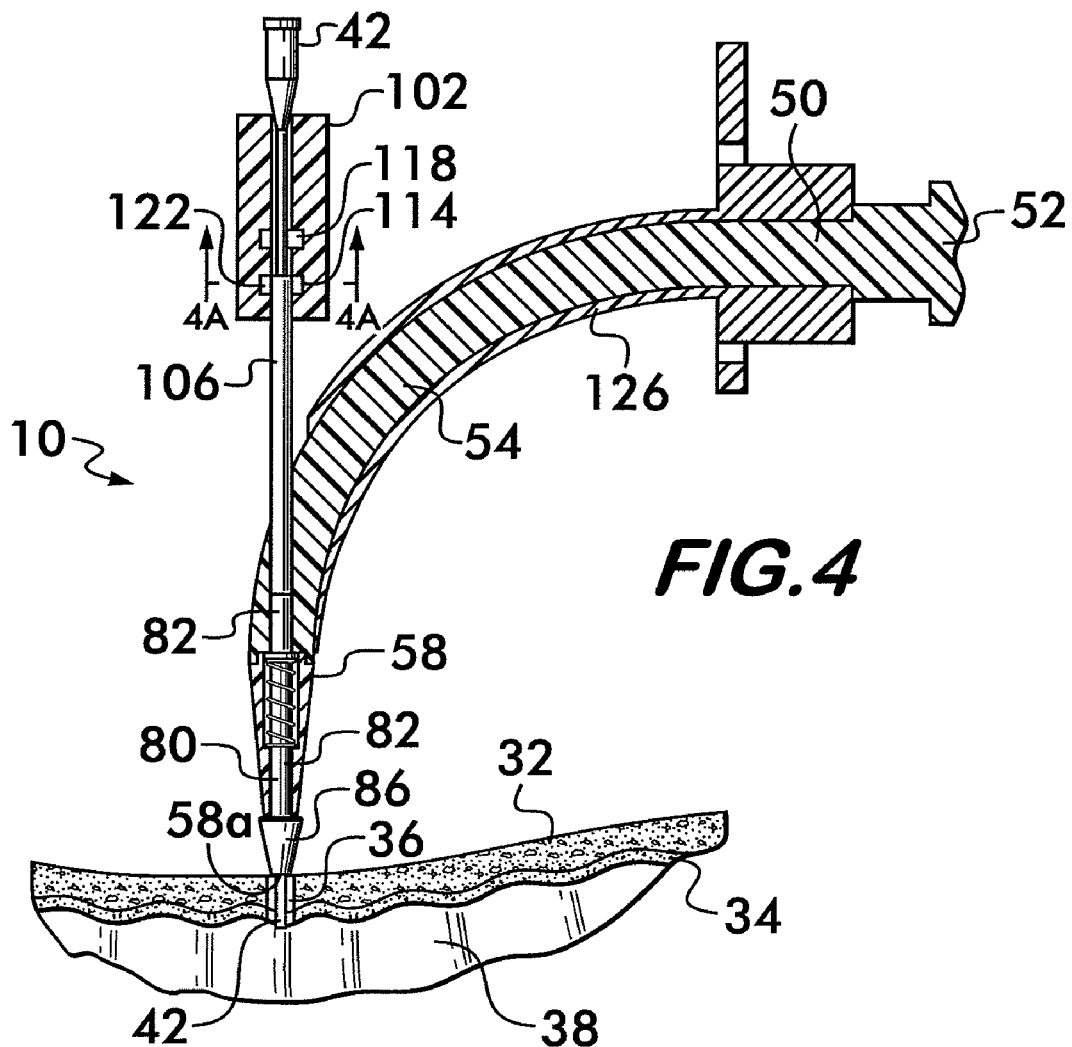
FIG. 4 is an elevational view, partially in section, of a device for performing a tracheostomy of the present invention illustrating the needle and syringe removed from the device and the remaining catheter protruding into the trachea of the patient.

Referring again to FIG. 2A, within the internal cavity 70, there is disposed on the linear shaft 82 a stop 90 which restricts proximal and distal movement of the tracheal anchor 80 to the length of the internal cavity 70. Also within the internal cavity 70, a spring 94 is disposed over the linear shaft 82. As best shown in FIG. 4, the spring 94 biases the tracheal anchor 80 to a normally retracted position, whereupon the anchor tip 86 of the tracheal anchor 80 rests upon the opening 58a of the tapered piece 58 (FIGS. 5 and 6).

Referring now to FIGS. 1, 4 and 5, a driver mechanism 98 includes a cylindrical twister component 102 and a rod-like pusher component 106. As best shown in FIGS. 4 and 5, the pusher component 106 is arranged to extend into the internal passageway 62 of the curved body portion 54 and abut the upper end of the linear shaft 82. In response to a user pressing down on the driver mechanism 98, the tracheal anchor 80 is caused to move from the retracted position (FIG. 4) to an extended position as best seen in FIG. 5. As shown in FIG. 5, when the tracheal anchor 80 is caused to move to the extended position, the spring 94 moves into a compressed state. In this manner, the anchor tip 86 may be driven through the opening 36 in the patient's neck and into the trachea 38. However, as discussed above, movement of the tracheal anchor 80 is limited to prevent piercing of the posterior wall of the trachea 38 during insertion. The length of extension of the anchor tip 86 is determined based upon the human anatomy of the trachea 38 and its location within the neck of the human population.

Referring again to FIG. 3, the twister component 102 includes an open internal passageway 102a as does the pusher component (not shown). These open internal passageways are coaxial in such a manner as to permit passage of the needle 30 and catheter 42 therethrough. Referring now to FIGS. 2 and 3, the open internal passageway 102a of the twister component 102 includes a plurality of shelves or landings. For example, two such shelves or landings are shown at 114 and 118. The proximal end of the pusher component 106 is arranged to extend within the open internal passageway 102a of the twister component 102.

Figure 3A:
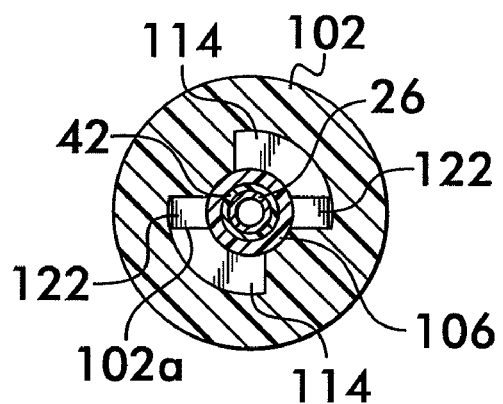
FIG. 3A is a sectional view taken along lines 3A-3A of FIG. 3.

At its proximal end, the pusher component 106 includes wings 122. The wings 22 enable the pusher 106 and twister 102 to adjust between an unlocked position (best shown in FIGS. 2, 3 and 3A) and a locked position (best shown in FIGS. 4 and 4A). As will be described in more detail below, during insertion of the needle 30 and catheter 42 into the trachea 38, the pusher 106 and twister 102 are situated in the unlocked position, thus allowing the pusher 106 to move freely within the internal passageway of the twister 102 so as to prevent insertion of the anchor tip 86 during needle insertion. After the needle has been withdrawn, the pusher and twister are then moved to the locked position for insertion of the anchor tip 86 into the trachea 38, the pusher and twister are situated in the locked position.

Figure 4A:
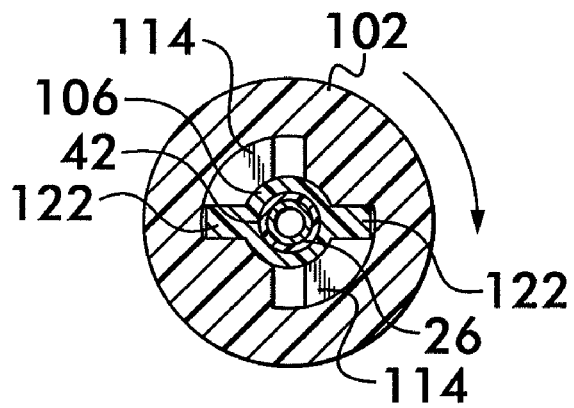
FIG. 4A is a sectional view taken along lines 4A-4A of FIG. 4.

As best shown in FIGS. 4 and 4A, when the wings 122 are seated within shelf 114, the pusher component 106 becomes locked within the twister component 102. Likewise, when the wing 122 is seated within the shelf 118 (this arrangement not shown), locking occurs. By seating the wings 122 within shelf 114, the resulting driver mechanism 98 is longer than if the wings 122 were seated in shelf 118. By adjusting the length of the driver mechanism 98, one can adjust the depth to which the anchor tip 86 is driven within the neck of a patient to assure entry into the trachea 38. The anatomy of the human neck varies from patient to patient. By providing shelves 114 and 118, a user of the device 10 may adjust the length of the driver mechanism 98 from shorter to longer (or vice versa) to drive the anchor tip 86 to a lesser or greater depth within the neck to reach the trachea 38. For example, on the majority of patients, the trachea 38 can be reached by situating the wing 122 within the shelf 118. For the remaining minority of patients, the trachea 38 can be reached by situating the wing 122 within the shelf 114. In this manner, depth of penetration into the trachea can be controlled to minimize the possibility for piercing the posterior wall thereof.

Although the embodiment 10 illustrates use of a driver mechanism 98 comprised of the locking and unlocking pusher and twister components, 106 and 102, respectively, the driver mechanism 98 is an optional part for driving the anchor tip 86 into the trachea 38. For example, in a non-emergency setting, such as within a hospital where time is less critical, use of the driver mechanism 98 to seat the anchor tip 86 within the trachea 38 may help reduce the risk of injury to the posterior wall of the trachea 38, esophagus, and/or larynx. However, under emergency conditions where a patient's life may be at risk and time may be limited, a paramedic or other emergency medical professional may choose to forego use of the driver mechanism 98. Under these circumstances, it is possible for such a professional to drive the anchor tip 86 into the trachea 38 by simply pushing down on the handle 52.

Referring now to FIG. 6, once the anchor tip 86 is inserted and breaches through the cartilage forming the trachea 38, the user, e.g., a doctor or other emergency medical professional, will hear a popping sound and feel a loss of resistance, thus providing assurance that the tracheal anchor 80 is properly located within the trachea 38 and there is no need to advance further. The anchor tip 86 will spring load upwardly and become lodged between the rings of the trachea 38 (e.g., between either the first and second, or the second and third tracheal rings). The spring-loading feature of the tracheal anchor 80 prevents its further advancement into the trachea 38, thus avoiding possible damage to the posterior wall thereof.

Referring now to FIG. 7, a tracheostomy tube 126 is shown disposed over the curved body portion 54 of the tracheostomy dilator 46. Once the tracheal anchor 80 is inserted within the trachea 38, by utilizing the handle 52, the curved body portion 54 of the tracheostomy dilator 46 may be inserted into the trachea 38 to enlarge the opening 36 to allow the tracheostomy tube 126 to pass therethrough and into the trachea 38. The curved body portion 54 of the tracheostomy dilator 46 is shaped to extend down and follow the natural path of the trachea 38 of a patient and is shaped to avoid piercing the posterior wall of the trachea 38.

As best shown in FIG. 1, the handle 52 is provided with a plurality of finger grips 56 and a thumb grip 57 to facilitate passage of the tracheostomy dilator 46 into the trachea 38 to gradually widen the opening 36 therein. The tracheostomy dilator 46 may then be withdrawn from the trachea 38 by drawing back on the handle 52 while retaining the tracheostomy tube 126 within the opening in the trachea 38. If suitable, the tracheostomy tube 126 may then be strapped to the patient's neck to ensure proper placement. The embodiment 10 could be provided in pieces in kit form ready to be quickly assembled when needed in an emergency.

In use, the technician must first determine the proper site on the patient's neck for performing the tracheostomy. Typically the site is located approximately two centimeters (or two finger breadths) above the sternal notch on the neck of the patient. Once located, the site is sterilized using an alcohol swab or using any other suitable antiseptic. An incision is then made at the site using a scalpel approximately 2 centimeters in size. The incision is made in the vertical direction. Optionally, especially in the case of an obese person, a hemostat or similar instrument may be used to separate and lay open the skin layers at the site of the incision.

Next, the tracheostomy dilator 46 is attached to the handle 52 and the needle 30 and catheter 42 are attached to the syringe 14. The tracheostomy dilator 46 is then placed over the incision site. Next, the driver mechanism 98 is assembled by placing the pusher component 106 within the twister component 102 and placing the components in the unlocked position as described above. As best shown in FIGS. 2 and 6, the assembled driver mechanism 98, i.e., the pusher 106 and twister 102, is then inserted through the opening 66 located on the outer surface of the curved body portion 54 until the distal end of the pusher 106 abuts the upper end of the linear shaft 82 of the tracheal anchor 80. The needle 30, with the catheter 42 surrounding it, is then inserted through the coaxially aligned open passageways of the twister 102, pusher 106, and open channel of the tracheal anchor 80. With the tracheostomy dilator 46 placed over the incision site, the needle 30 and catheter 42 may be inserted through the incision site 36 and into the trachea 38.

Referring now to FIGS. 1 and 3, the thumbhold 20 may be utilized to withdraw the plunger 18 to aspirate air through the needle tip 30*a* to validate proper placement of the needle 30 and catheter 42 within the trachea 38. Next the needle 30 and syringe 14 are removed leaving the catheter 42 in place within the trachea 38. The catheter 42 is made of a resilient material and will not puncture or otherwise damage the wall of the trachea 38. The catheter 42 will serve in the place of a guide wire of the prior art for inserting the anchor tip 86.

Next, as discussed in detail above, the pusher 106 and twister 102 are rotated from the unlocked position to an appropriate locked position by inserting the wing 122 of the pusher 102 into either shelf 114 or 118 within the internal passageway of the twister 106. The driver mechanism 98 is then utilized to drive the spring-loaded anchor tip 86 of the tracheal anchor 80 over the catheter 42 and through the opening 36 and into the trachea 38. As best shown in FIG. 5, as the anchor tip 86 passes through the opening 36 in the neck and into the trachea 38, the spring 94 is in compression. As best shown in FIG. 6, once the anchor tip 86 has entered the trachea 38 and the driver mechanism has been removed from the internal passageway 62, the spring 94 will expand from its compressed state and will pull the anchor tip 86 up against the rings of the trachea 38. Once the anchor tip 86 has penetrated into the trachea 38, a popping sound may be heard and the user may experience a loss of resistance to confirm that the anchor tip 86 is within the trachea 38. Optionally, once the anchor tip 86 is seated within the trachea, a syringe 14 may be attached to the catheter 42 to aspirate to confirm that the anchor tip 86 has been properly located within the trachea 38.

Referring now to FIGS. 7 and 8, after the catheter 42 and the driver mechanism 98 have been removed from the internal passageway 66, the remaining portion of the tracheostomy dilator 46 may then be passed through to enlarge the opening 36 though the trachea 38. The tracheostomy dilator 46 is inserted into the trachea 38 until the tracheostomy tube 126 is inserted within the opening in the trachea 38. The tracheostomy dilator 46 including the anchor tip 86 is then withdrawn from the opening 36 while the tracheostomy tube 126 is held in place. The tracheostomy tube 126 is attached to a suitable ventilation source and, if suitable, held in place with straps to ensure proper placement.

Figure 9:
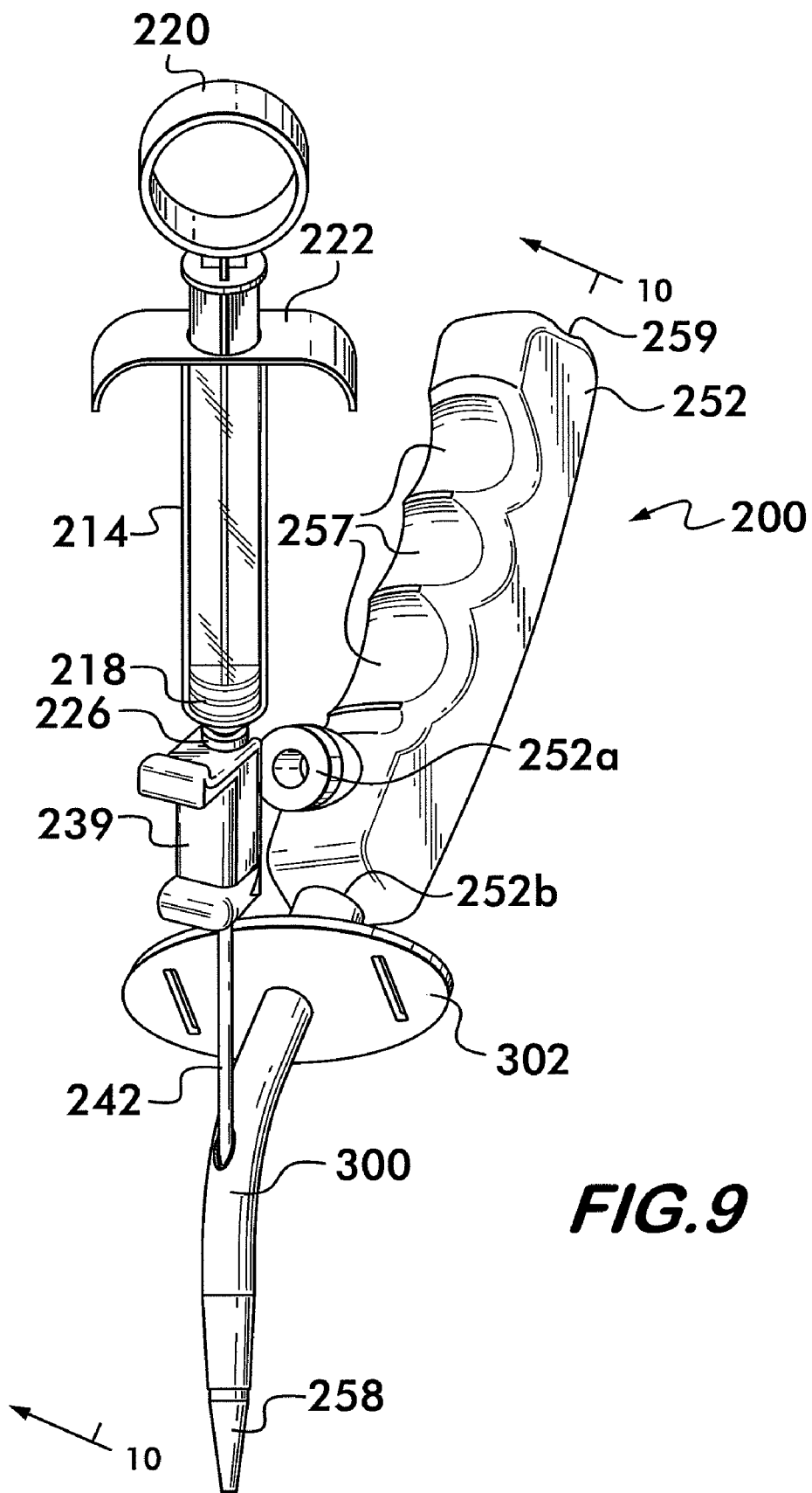
FIG. 9 is a perspective view of a device for performing a cricothyroidotomy of the present invention.
Figure 10:
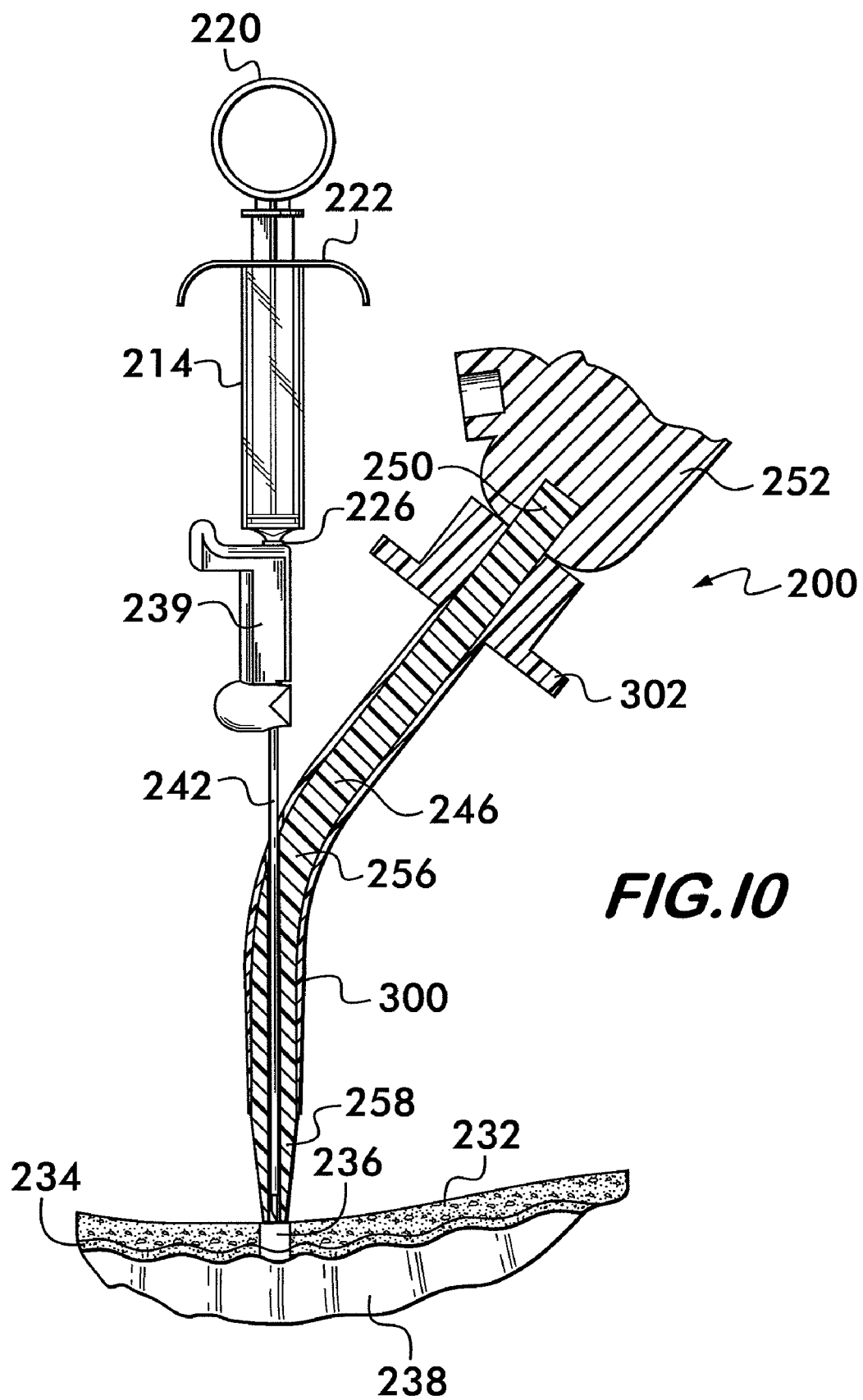
FIG. 10 is a sectional view taken along lines 10-10 of FIG. 9.
Figure 11:
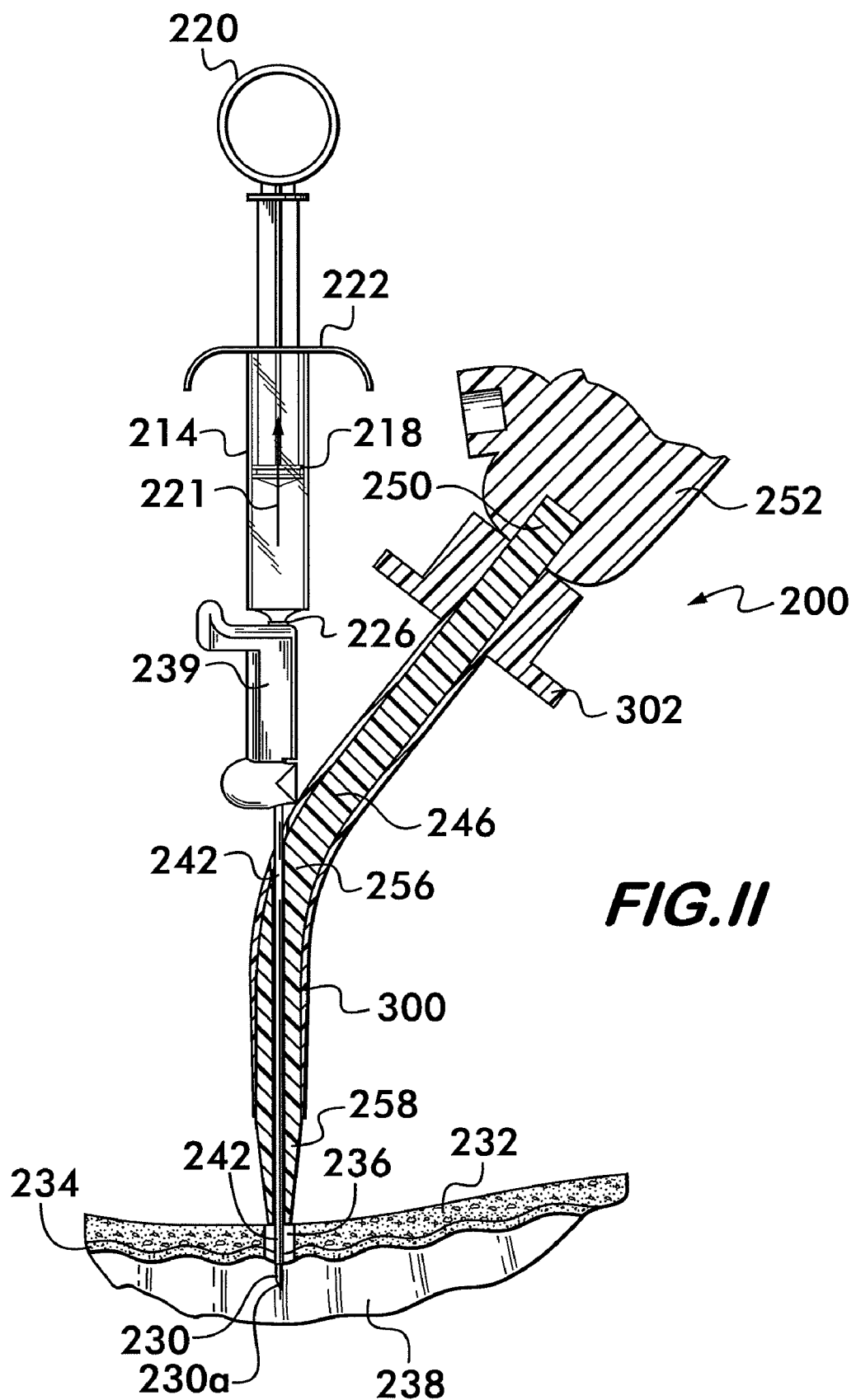
FIG. 11 is an elevational view, partially in section, of a cricothyroidotomy device of the present invention illustrating the needle and catheter extending into the trachea of a patient.

Referring now to FIGS. 9 through 15, there is shown at 200 an embodiment of the present invention for performing an emergency cricothyroidotomy. As shown in FIG. 9, the device 200 comprises a syringe 214. The syringe 214 includes a movable plunger 218 which is capable of movement along the cylindrical length of the syringe 214. The plunger 218 is also removable from the syringe 214 at end 222 and includes a thumbhold 220 to enable withdrawal of the plunger 218 using the thumb of the same hand that is manipulating the syringe 214. Referring now to FIG. 11, a needle 230 is attached at the other end of the syringe 214. The needle 230 includes a sharpened distal end 230*a* to penetrate the cricothyroid membrane which is the site of entry for performing the cricothyroidotomy. Positioned over the needle 230 is a flexible catheter 242, preferably made from teflon or another suitable resilient material. The safety limiter 239 is arranged to snap over the catheter 242.

During the cricothyroidotomy, the patient's chin is rotated away from his or her chest, exposing the neck and causing the trachea 238 to move closer to the skin. Next, the site of the cricothyroidotomy is located. The cricothyroidotomy may be performed at the cricothyroid membrane 234 which may be found by touch. That is, the person performing the procedure feels the skin of the patient and probes with a finger for an indentation in the cricoid cartilage (not shown). The cricothyroid membrane 234 is located in that indentation between the thyroid cartilage and the cricoid cartilage. Particularly in male patients, it may be advantageous to locate the Adam's apple by touch, and move slightly inferior to that in order to find the indentation.

As best shown in FIGS. 10 and 11, once the cricothyroid membrane 234 is located, an initial incision is made (approximately 2 centimeters in size) through the skin 232 and cricothyroid membrane 234 using a suitable scalpel. Thereafter, the needle 230 and catheter 242 may be inserted through the incision to penetrate the skin 232 and cricothyroid membrane 234 to create an opening 236 extending into the trachea 238. FIG. 10 shows the position of the safety limiter 239 prior to insertion of the needle 230 and catheter 242 and FIG. 11 shows the position of the limiter 239 after insertion of the needle and catheter. As shown in FIG. 11, during insertion, the safety limiter 239 eventually abuts the outer surface of a tracheotomy tube 300 disposed over a dilator 246. The abutting relationship between the safety limiter 239 and the tube 300 serves as a stop to regulate the distance the needle 230 may travel into the trachea 238 to prevent puncture of the soft posterior wall of the trachea 238. The anatomy of the trachea 238 as well as its location within the neck will dictate the overall length of the safety limiter 239. Likewise, the question of whether to use the safety limiter 239 during an emergency cricothyroidotomy is dictated by the trachea anatomy and its location within the neck of a patient.

For example, with the safety limiter 239 in place, the needle 230 may be inserted through the neck to a safe and proper position within the trachea 238 without causing injury in approximately 80%-90% of the population. For the remaining 10%-20% of patients, where the location of the trachea falls outside this range, the safety limiter 239 may be removed prior to insertion of the needle within the trachea 238. Although use of this embodiment 200 without the safety limiter 239 may compromise safety and possibly increase the risk of injury, such an approach may be necessary where emergency circumstances require it.

Referring again to FIG. 11, to affirm that the needle 230 is within the trachea 238, the plunger 218 may be withdrawn utilizing the thumbhold 220 in the direction of arrow 221 to determine the nature of the material at the needle tip 230a. If little or no blood is drawn into the chamber of the syringe 214 and there is aspiration of air, it can be assumed that the needle tip 230a is positioned correctly within the trachea 238. Once this has been ascertained, the needle 230 and syringe 214 may be removed from the opening 236 with the catheter 242 remaining therein.

The embodiment 200 includes a dilator 246, which is shown in FIGS. 10-14. The dilator 246 includes a proximal end 250 which is arranged for attachment to a handle 252, such as when parts of the device 200 are being provided in kit form. Alternatively, the dilator 246 and handle 252 may be of integral construction. The handle 252 is of the same construction as handle 52 discussed in the first embodiment 10. The handle 252 is provided with a first attachment point 252a (FIG. 9) for attachment to dilator 46 when used during an emergency tracheostomy, and a second attachment point 252b (FIG. 9) for attachment to dilator 246 (FIG. 10) when used for an emergency cricothyroidotomy. In this manner, the same handle can be used for both procedures.

As shown in FIGS. 10-14, the dilator 246 also includes a curved portion 256 and a tapered distal end 258 for entering within the opening 236. The proximal end 250 and curved portion 256 are shown as being of uniform cross-section. However, other geometries may be employed without departing from the scope of the invention. The dilator 246 may be hydrophobically coated or coated with a suitable surgical lubrication.

Referring now to FIGS. 9-14, a tracheotomy tube 300 is shown disposed over the dilator 246. Once the dilator 246 is inserted within the trachea 238, by utilizing the handle 252, the dilator 246 may be inserted further into the trachea 238 to enlarge the opening 236 to allow the tube 300 to pass therethrough and into the trachea 238. Thereafter, the catheter 242 may be removed. The wall of the tube 300 is sufficiently tapered at its distal end to avoid any abrupt widening of the opening 236 as the tube is passed into the trachea 238. The dilator 246 is shaped to extend down and follow the natural path of the trachea 238 of a patient and is shaped to avoid piercing the posterior wall thereof.

As best shown in FIG. 9, the handle 252 is provided with a plurality of finger grips 257 and a thumb grip 259 to facilitate passage of the dilator 246 into the trachea 238 to gradually widen the opening 236 therein. The dilator 246 may then be withdrawn from the trachea 238 by drawing back on the handle 252 while retaining the tube 300 within the opening in the trachea 238. If appropriate under the circumstances, the tube 300 may then be strapped around the patient's neck to ensure proper placement. The embodiment 200 could be provided in pieces in kit form ready to be quickly assembled when needed in an emergency.

Figure 12:
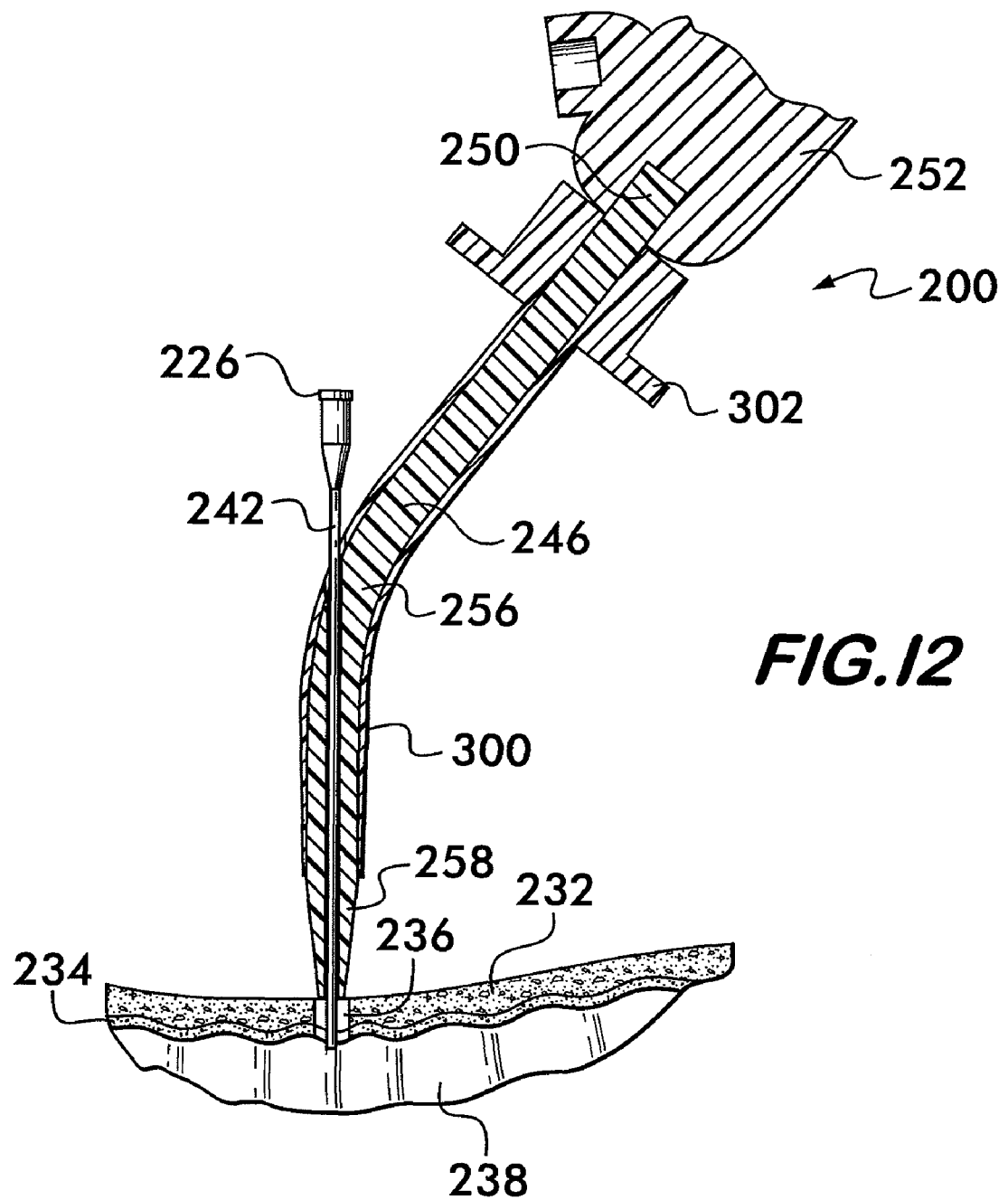
FIG. 12 is an elevational view, partially in section, of a cricothyroidotomy device of the present invention illustrating the needle and syringe removed from the device and the catheter remaining within the trachea of the patient.

In use, the technician must first determine the site of the patient's cricothyroid membrane 234. Once located, the site is sterilized using an alcohol swab or using any other suitable antiseptic. An incision is then made in the cricothyroid membrane 234 using a scalpel approximately 2 centimeters in size. The incision is made in the vertical direction. Next, the dilator 246 is attached to the handle 252 and the needle 230 and catheter 242 are attached to the syringe 214. The safety limiter 239 is snapped over the catheter 242. The dilator 246 is then placed over the incised cricothyroid membrane 234. The needle 230 and catheter 242 are then inserted through an open passageway 262 (FIG. 13) of the dilator 246. As best shown in FIG. 11, with the dilator 246 placed over the incision site, the needle 230 and catheter 242 may then be inserted through the skin 232 and the cricothyroid membrane 234 and into the trachea 238. The thumbhold 220 may then be withdrawn in the direction of arrow 221 to aspirate air through the needle tip 230a to validate proper placement of the needle 230 and catheter 242 within the trachea 238. As best shown in FIG. 12, the needle 230 and syringe 214 are next removed, leaving the catheter 242 in place within the trachea 238.

Figure 13:
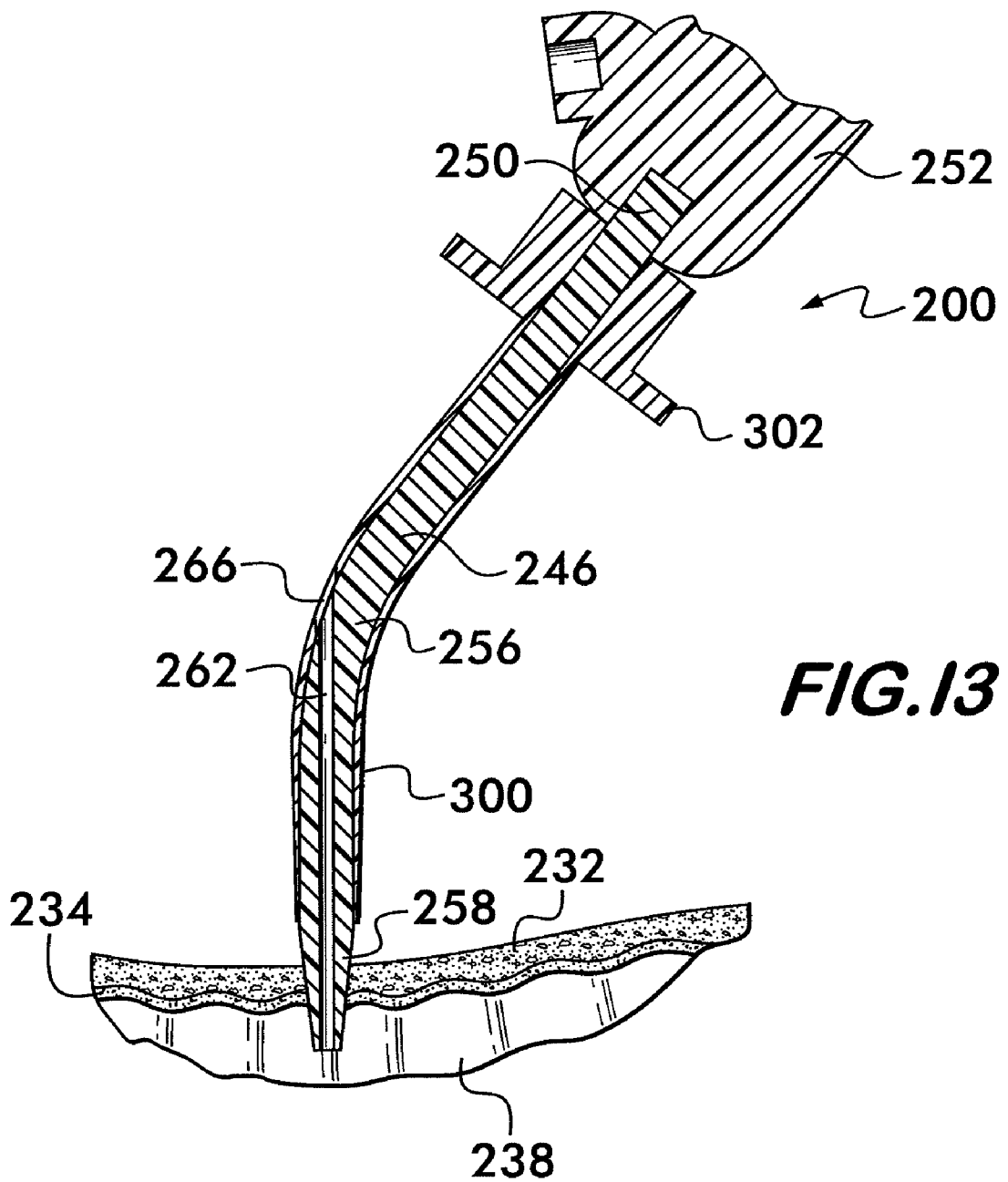
FIG. 13 is an elevational view, partially in section, of a cricothyroidotomy device of the present invention illustrating the dilator extending into the opening in the trachea of the patient.
Figure 14:
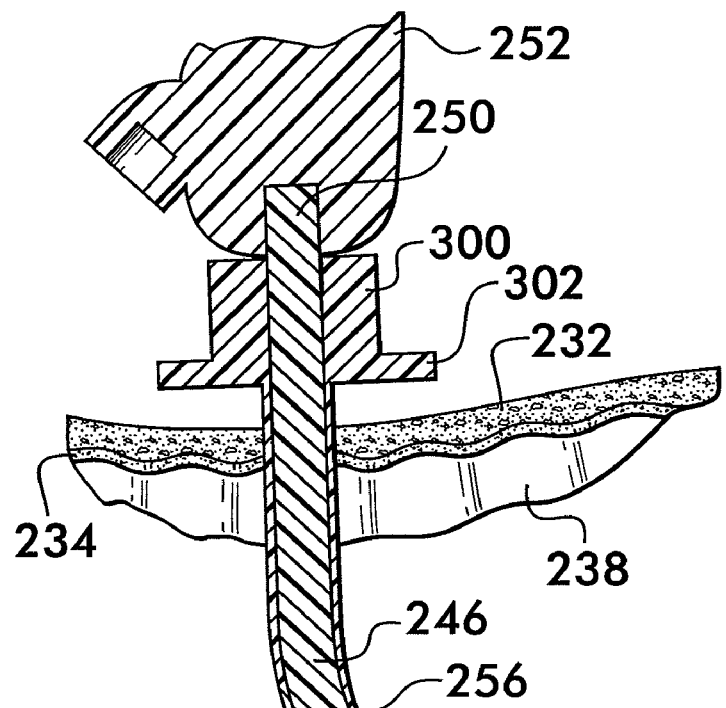
FIG. 14 is an elevational view, mostly in section, of the dilator and tracheostomy tube components of a cricothyroidotomy device of the present invention advanced into the opening in the trachea of the patient.
Figure 15:
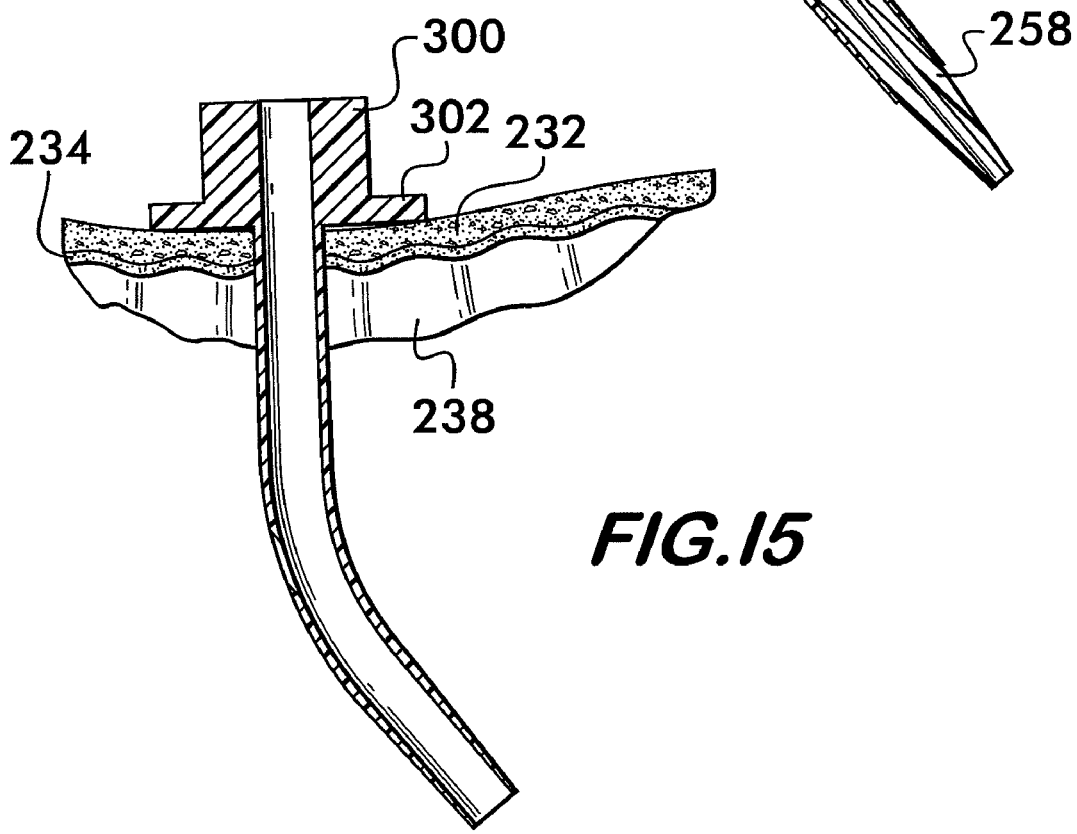
FIG. 15 is an elevational view, in section, of the tracheotomy tube component of a cricothyroidotomy device of the present invention advanced into the opening in the patient's trachea with the dilator having been removed.
Figure 18:
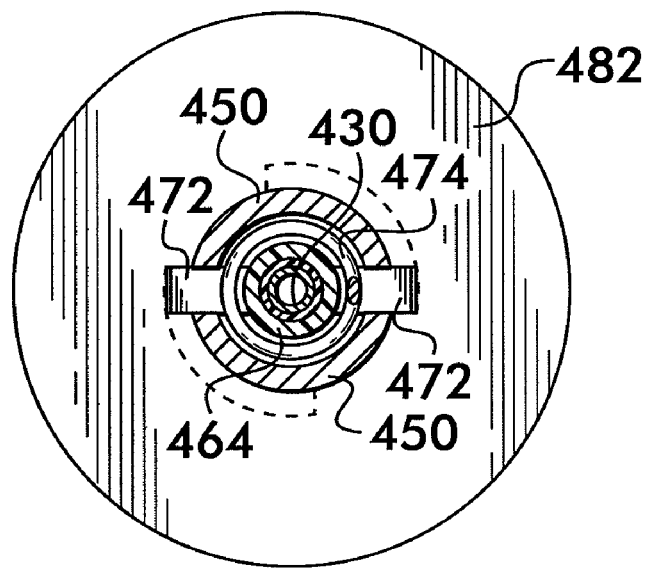
FIG. 18 is a sectional view taken along lines 18-18 of FIG. 17.
Figure 19:
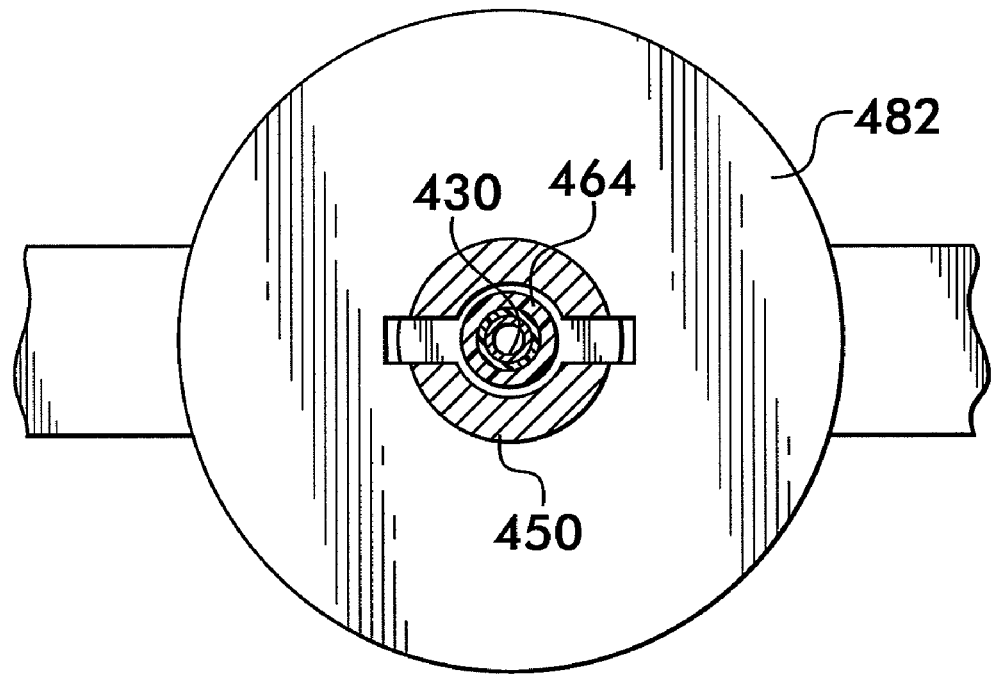
FIG. 19 is a sectional view taken along lines 19-19 of FIG. 17.

Referring now to FIGS. 12, 13, and 14, the dilator 246 may then be passed through to enlarge the opening 236 though the trachea 238 and the catheter 242 is removed. As best shown in FIG. 14, the dilator 246 is inserted into the trachea 238 until the tube 300 is inserted down within the opening in the trachea 238. As best shown in FIG. 15, the dilator 246 is then withdrawn from the opening 236 with the tube 300 remaining in place for connection to a suitable source for ventilation (not shown). If suitable, the tube 300 may be held in place by attaching straps to wings 302 located on the tube 300.

Referring now to FIGS. 16 through 25, there is shown at 400 a third embodiment of the present invention which is arranged for performing an emergency tracheostomy. As shown in FIGS. 16, 17, and 20, the device 400 comprises a syringe 414 which includes a movable plunger 418 which is capable of movement along the cylindrical length of the syringe 414. The plunger 418 is also removable from the syringe 414 at end 422 and includes a thumbhold 420 to enable withdrawal of the plunger 418 using the thumb of the same hand that is manipulating the syringe 414. Referring now to FIG. 20, at the other end of the syringe 414, a needle 430 is attached thereto. The needle 430 includes a sharpened distal end 430a to penetrate the skin 432 and cartilage 434 forming the wall of the trachea 438 just above the sternal notch (not shown) at the site of entry where the tracheostomy is performed. Positioned over the needle 430 is a flexible catheter 442, preferably made from teflon or another suitable resilient material.

Referring again to FIG. 16, the embodiment 400 also includes a stationary base portion 446 having a central opening. The base portion 446 includes wings 446a and is arranged for placement at the site of entry for a tracheostomy. Extending upwardly from the base portion 446 is a hollow tube portion 450, which also remains stationary during the tracheostomy procedure. Together, the central opening of the base portion 446 and the hollow tube portion 450 form an internal passageway 454 (FIG. 17) extending from the base portion 446 through the tube portion 450. The passageway 454 is open at both ends. In addition, the tube portion 450 includes a pair of opposed slots 458 that extend vertically the length of the tube portion 450. One of the two slots 458 is best illustrated in FIG. 16.

Disposed within the internal passageway 454 is a tracheal anchor 464. The tracheal anchor 464 includes a rod-like shank which has at its distal end a conically-shaped anchor tip 468 which actually extends outside the open internal passageway 454 at the bottom of the base portion 446. The anchor tip 468 is arranged for insertion through the opening 436 in the neck and into the trachea 438. At its proximal end, the tracheal anchor 464 includes a pair of opposed wings 472. During use of this embodiment 400, the opposed wings 472 are arranged to move within the pair of vertical slots 458 extending the length of the tube portion 450.

The tracheal anchor 464 is provided with an open internal channel (not shown) which runs axially along its entire length to allow passage of the needle 430 and the catheter 442 therethrough. The hollow tube portion 450 includes a pocket for retaining a spring 474 therein, the spring 474 being disposed over and retained to the tracheal anchor 464. As best shown in FIG. 22, the spring 474 disposed within the pocket of the hollow tube portion 450 biases the tracheal anchor 464 to a normally retracted position, whereupon the anchor tip 468 rests upon the distal opening of the internal passageway 454. The spring 474 restricts movement of the tracheal anchor 464 between the retracted position just described and an extended position, as shown, for example, in FIG. 23, where the anchor tip 468 is driven through the opening 436 in the patient's neck and into the trachea 438. As shown in FIG. 23, when the tracheal anchor 464 moves to the extended position, the spring 474 moves to a compressed state within the pocket to preclude further distal movement of the anchor tip 468. In this manner, movement of the tracheal anchor 464 is limited or restricted to prevent piercing of the posterior wall of the trachea 438 during insertion. The length of extension of the anchor tip 468 is determined based upon the human anatomy of the trachea 438 and location of the trachea 438 within the neck of the human population.

Referring now to FIGS. 16, 17, 22, and 23, a twister 482 includes an opening at the top thereof as indicated at 483 (FIG. 16) to allow passage of the needle 430 and the catheter 442 therethrough. The twister 482 also includes an internal passageway at 482a. As best shown in FIGS. 17 and 22-25, the proximal end of the tube portion 450 is arranged to extend within the internal passageway 482a of the twister 482. The twister is arranged to move axially over the proximal end of the tube portion 450 during insertion of the needle 430 and catheter 442 into the trachea 438 as well as during insertion of the anchor tip 468 into the trachea 438.

Referring now to FIGS. 22 and 23, as described in the first embodiment 10, the internal passageway 482a of the twister 482 includes a plurality of shelves or landings in which the opposed wings 472 of the tracheal anchor 464 may be seated to lock the twister 482 and with the tracheal anchor 464 together. Optionally, the shelves or landings may include a pair of lower landings and a pair of upper landings, as described at 114 and 118, respectively, in the first embodiment 10. Thus, the tracheal anchor 464 and twister 482 may be adjusted between an unlocked position (best shown in FIGS. 20 and 21) and a locked position (best shown in FIGS. 22 and 23). As will be described in more detail below, during insertion of the needle 430 and catheter 442 into the trachea 438, the tracheal anchor 464 and twister 482 are situated in the unlocked position. By contrast, once the catheter 442 is in place within the trachea 438 to drive the anchor tip 468 into the trachea 438, the tracheal anchor 464 and twister 482 are moved from the unlocked position to the locked position.

Referring now to FIG. 24, once the anchor tip 486 breaches through the cartilage forming the trachea 438, a popping sound and/or feel a loss of resistance may be experienced, thus providing assurance that the anchor tip 468 is properly located within the trachea 438. As described under the first embodiment 10, upon entry into the trachea 438, the anchor tip 468 will spring load upwardly and become lodged between the rings of the trachea 438, thus avoiding possible damage to the posterior wall of the trachea 438.

Once the anchor tip 468 is lodged between the rings of the trachea 438, the twister 482 may be unlocked and removed, while leaving the base portion 446 and tracheal anchor 464 in place within the trachea 438 for connection to a ventilation source (not shown).

In use, the proper site on the patient's neck for performing the tracheostomy must be located, sterilized and incised. The base portion 446 is placed over the incision site with the passageway 454 directly over the incision site. Next, the needle 430 and catheter 442 are attached to the syringe 414 and passed through the open top 483 of the twister 482 and through the open internal channel of the tracheal anchor 464, the tracheal anchor 464 already being disposed within the central passageway 454 of the base portion 450. The twister 482 and tracheal anchor 464 are maintained in the unlocked position.

As best shown in FIG. 20, the needle 430, with the surrounding catheter 442, are then inserted in the direction of arrow 443 through the incision site 436 and into the trachea 438. By comparing FIGS. 17 and 20, it is demonstrated that during insertion of the needle and catheter into the trachea 438, the twister 482 moves axially over the hollow tube portion 450 in the direction of arrow 443. Because the tracheal anchor 464 is unlocked from the twister 482, it does not move axially during insertion of the needle 430 and catheter 442. Referring now to FIG. 21, the thumbhold 420 may be utilized to aspirate air through the needle tip 430a to validate proper placement of the needle 430 and catheter 442 within the trachea 438. Thereafter, the needle 430 and syringe 414 are removed leaving the catheter 442 in place within the trachea 438. As in earlier embodiments, the catheter 442 is made of a resilient material and will not puncture or otherwise damage the wall of the trachea 438 and serves as a guide for inserting the anchor tip 468.

Referring now to FIG. 22, the twister 482 is next rotated in the direction of arrow 485 from the unlocked position to an appropriate locked position with respect to the tracheal anchor 464. Referring now to FIG. 23, the twister 482 is then utilized to drive the tracheal anchor 464, including the anchor tip 468 through the opening 436 and into the trachea 438. As the tracheal anchor 464 moves axially through the tube portion 450, the wings 472 travel through the opposed slots 458 extending vertically over the length of the tube portion 450. As shown in FIGS. 22 and 23, as the anchor tip 468 passes through the opening 436 in the neck and into the trachea 438, the spring 474 moves into compression. As best shown in FIG. 24, and as described in the first embodiment 10, once the anchor tip 468 has entered the trachea 438, the spring 474 will move from its fully compressed state to a lesser compressed state to urge the anchor tip 468 against the rings of the trachea 438. Referring now to FIG. 25, once the anchor tip 468 is seated against the rings of the trachea 438, the twister 482 may be unlocked by rotating in the direction opposite arrow 485 in FIG. 22 and removed to enable attachment of the tracheal anchor 464 to a suitable source for ventilation of the patient (not shown). If suitable, the base portion 446 may be held in place with straps attached to the wings 446a to ensure proper placement.

The foregoing description and accompanying drawings should be considered as illustrative only of the principles of the invention. The invention may be configured in a variety of ways and is not intended to be limited by the preferred embodiments or methods. Numerous applications of the invention will readily occur to those skilled in the art from a consideration of the foregoing description. Therefore, it is desired that the invention not be limited to the specific example disclosed or the construction and operation shown and described. Rather, all suitable modifications and equivalents may be resorted to, falling within the scope of the invention.

What is claimed is:

1. A device for performing a tracheostomy comprising:
   a. a dilator having a distal end arranged for insertion into a trachea and a proximal end arranged to remain outside the trachea, the distal end including an aperture arranged for placement at a location on the neck of a patient for performing the tracheostomy, said dilator additionally comprising a generally curved outer surface extending between the distal and proximal ends;
   b. an open generally linear passageway extending within said dilator from said distal aperture to a port positioned proximally along the curved outer surface of said dilator;
   c. an anchor retained within said open passageway, said anchor including a distal tip portion protruding through said distal aperture, said anchor normally biased to a retracted position and arranged to move from said retracted position to an extended position in response to a distal force; and,
   d. a driver for applying said distal force to said anchor to drive said distal tip portion through an opening in the patient's neck and trachea.

2. The device of claim 1, wherein said distal tip portion is pointed and sharp.

3. The device of claim 1, wherein said dilator includes a tapered distal end.

4. The device of claim 3, wherein said dilator is arranged for insertion down the patient's trachea to expand the size of the opening in the trachea after the distal tip portion of the anchor has penetrated the trachea.

5. The device of claim 4, additionally comprising a tracheostomy tube arranged to be disposed over the curved outer surface of said dilator, said tracheostomy tube arranged to be disposed within the trachea opening and remain therein after the dilator has been removed, said tracheostomy tube providing a point for delivering air flow into the patient's trachea.

6. The device of claim 5, wherein said tracheostomy tube additionally comprises an inflatable cuff.

7. The device of claim 1, which may be carried by a person in a disassembled configuration, and may be used to perform tracheostomies in an assembled configuration.

8. The device of claim 1, wherein the curvature of the outer surface of the dilator fits the curvature of a trachea of a patient.

9. The device of claim 1, wherein said distal tip portion is configured to extend through an opening in the patient's neck and trachea, wherein the opening in the neck of a patient leading into the trachea is between adjacent cartilage rings on the trachea.

10. The device of claim 1, additionally comprising a needle positioned in said port, said needle having a hollow passageway therein and having a sharp tip adapted to penetrate through tissue in the neck and into the trachea to create the opening in the patient's neck and trachea.

11. The device of claim 10, further comprising a tubular catheter surrounding said needle, said catheter arranged to remain within the trachea after the needle has been removed therefrom.

12. The device of claim 11, wherein, said driver and said anchor include open internal passageways that are coaxial with each other, and wherein said needle and said catheter are arranged to pass through said coaxial open passageways when creating the opening in the patient's neck and trachea.

13. The device of claim 12, further comprising a syringe connectable to said needle and having a chamber communicating with said hollow passageway of said needle when said syringe is connected to said needle.

14. The device of claim 1, additionally comprising a mechanism disposed on said anchor for biasing said anchor towards said retracted position.

15. The device of claim 14, wherein said mechanism is a spring.

16. The device of claim 12, wherein together said driver and said anchor form a stop to limit the distance said needle may extend into the trachea.

17. The device of claim 1, wherein said driver includes a twister component and a pusher component, a portion of said pusher component being disposed within said twister component, the pusher and twister components being arranged to move from an unlocked condition to a locked condition.

18. The device of claim 1, further comprising a handle attached to said dilator at its proximal end, said handle being shaped for grasping and manipulating said device during use.

19. The device of claim 1, wherein said driver is arranged for insertion through said port and through said open passageway to apply distal force against said anchor.

20. The device of claim 1, wherein said device is arranged for use on an emergency or non-emergency basis.

* * * * *